United States Patent
Yan et al.

(10) Patent No.: US 12,334,750 B2
(45) Date of Patent: Jun. 17, 2025

(54) FAR-FIELD WIRELESS CHARGING OF MEDICAL DEVICES

(71) Applicant: Medtronic MiniMed, Inc., Northridge, CA (US)

(72) Inventors: Zhengchi Yan, Duarte, CA (US); Siddharth Chandra, Issaquah, WA (US); Emily A. Reveles, Northridge, CA (US); Sophia L. Wolf, Redondo Beach, CA (US); Arpit G. Christian, Chatsworth, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 707 days.

(21) Appl. No.: 17/644,014

(22) Filed: Dec. 13, 2021

(65) Prior Publication Data

US 2022/0216735 A1   Jul. 7, 2022

Related U.S. Application Data

(60) Provisional application No. 63/133,603, filed on Jan. 4, 2021.

(51) Int. Cl.
*H02J 7/00* (2006.01)
*A61B 5/00* (2006.01)
(Continued)

(52) U.S. Cl.
CPC ............ *H02J 50/20* (2016.02); *A61B 5/0531* (2013.01); *A61B 5/14532* (2013.01);
(Continued)

(58) Field of Classification Search
USPC .......................................... 320/108
See application file for complete search history.

(56) References Cited

U.S. PATENT DOCUMENTS 8,587,155 B2   11/2013   Giler et al.
8,810,195 B2 *  8/2014   Mochida ............ G06K 19/0701
                                                    320/108
(Continued)

FOREIGN PATENT DOCUMENTS

CN        106532984 A  *  3/2017

OTHER PUBLICATIONS

International Search Report and Written Opinion of International Application No. PCT/US2021/063619, dated Feb. 28, 2022, 12 pp.

*Primary Examiner* — Samuel Berhanu
(74) *Attorney, Agent, or Firm* — Weaver Austin Villeneuve & Sampson LLP

(57) ABSTRACT

Techniques are described for wirelessly charging a wearable or implantable medical device, such as a continuous glucose monitor (CGM) and/or an insulin pump. In some examples, the medical device includes: a rechargeable battery; a receiving antenna configured to wirelessly receive electrical power from a transmission antenna; charging circuitry configured to recharge the rechargeable battery using the electrical power received by the receiving antenna; and one or more processors configured to: determine a relative proximity of the medical device to a body of a patient; determine, based at least in part on the relative proximity, a tuning for the receiving antenna; and cause the receiving antenna to be tuned according to the determined tuning.

20 Claims, 9 Drawing Sheets

(51) Int. Cl.
    *A61B 5/0531*     (2021.01)
    *A61B 5/145*     (2006.01)
    *H02J 50/20*     (2016.01)
    *A61M 5/142*     (2006.01)

(52) U.S. Cl.
    CPC .... *A61B 5/6843* (2013.01); *A61B 2560/0219* (2013.01); *A61M 5/142* (2013.01); *A61M 2205/13* (2013.01); *A61M 2205/3306* (2013.01); *A61M 2205/3327* (2013.01); *A61M 2205/8206* (2013.01); *A61M 2205/8243* (2013.01); *A61M 2230/65* (2013.01)

(56) References Cited

U.S. PATENT DOCUMENTS

| | | |
|---|---|---|
| 8,888,744 B2 | 11/2014 | Yodfat et al. |
| 9,821,112 B2 * | 11/2017 | Olson ................. A61N 1/3787 |
| 9,824,815 B2 | 11/2017 | Leabman et al. |
| 2013/0342025 A1 | 12/2013 | Cook et al. |
| 2016/0277879 A1 | 9/2016 | Daoura et al. |
| 2017/0093168 A1 | 3/2017 | Von Novak, III et al. |
| 2017/0250566 A1 * | 8/2017 | Rudser ................ H02J 50/90 |
| 2017/0302090 A1 * | 10/2017 | Han ................ H02J 7/00308 |
| 2017/0373539 A1 | 12/2017 | Von Novak, III et al. |
| 2019/0009097 A1 * | 1/2019 | Hartley ................ H02J 50/80 |

* cited by examiner

FAR-FIELD WIRELESS CHARGING OF MEDICAL DEVICES

This application claims the benefit of U.S. Provisional Application Ser. No. 63/133,603, filed on Jan. 4, 2021, the entire contents of which are incorporated herein by reference.

TECHNICAL FIELD

This disclosure relates to medical systems and, more particularly, to wearable and implantable medical devices.

BACKGROUND

A patient may wear and/or be implanted with one or more medical devices, such as, but not limited to, a continuous glucose monitor (CGM) or an insulin pump. These types of medical devices may each include a removable or rechargeable battery to provide electrical power to operate the device.

SUMMARY

Various aspects of systems and techniques for wirelessly charging one or more wearable and/or implantable medical devices are described. In various examples of systems, a medical device includes a receiving antenna configured to wirelessly receive electrical power via far-field, microwave-spectrum electromagnetic waves in order to charge a rechargeable battery within the medical device. According to the techniques of this disclosure, the system is configured to dynamically control the recharging of the rechargeable battery.

As one example, a device is configured to monitor a relative proximity of the medical device to a body of a patient, and modify a tuning of the receiving antenna based on the monitored relative proximity. For example, the device may automatically "detune" the receiving antenna when the device determines that the medical device is relatively proximate to (e.g., in physical contact with or within a threshold distance of) the body of the patient. In some examples, detuning the antenna while the medical device is proximal to the patient may improve patient safety and comfort, such as by maintaining a comfortable temperature of the medical device, or in other words, by reducing a risk of the medical device overheating while positioned on or near the patient. In some examples, the device is configured to wirelessly charge the medical device according to other parameters, such as to maintain a minimum level of electrical charge in the rechargeable battery of the device or to enable simultaneous or near-simultaneous wireless charging of the rechargeable battery and operation of the functionality of the medical device.

In one example, the disclosure describes a medical device for having: a rechargeable battery; a receiving antenna configured to wirelessly receive electrical power from a transmission antenna; charging circuitry configured to recharge the rechargeable battery using the electrical power received by the receiving antenna; and one or more processors configured to: determine a relative proximity of the medical device to a body of a patient; determine, based at least in part on the relative proximity, a tuning for the receiving antenna; and cause the receiving antenna to be tuned according to the determined tuning.

In another example, the disclosure describes a system for system for wirelessly charging a medical device, the system including: a wireless-power-transfer device comprising a transmission antenna; and the medical device including: a rechargeable battery; a receiving antenna configured to wirelessly receive electrical power from the transmission antenna; charging circuitry configured to recharge the rechargeable battery using the electrical power received by the receiving antenna; and one or more processors configured to: determine a relative proximity of the medical device to a body of a patient; determine, based at least in part on the relative proximity, a tuning for the receiving antenna; and cause the receiving antenna to be tuned according to the determined tuning.

In another example, the disclosure describes a processor-implemented method for wirelessly charging a medical device via a receiving antenna, the method including: determining a relative proximity of a medical device to a body of a patient; determining, based at least in part on the relative proximity, a corresponding tuning for the receiving antenna of the medical device; and causing the receiving antenna to be tuned according to the corresponding tuning.

In another example, the disclosure describes one or more non-transitory processor-readable storage media storing instructions which, when executed by one or more processors, cause performance of: determining a relative proximity of a medical device to a body of a patient; determining, based at least in part on the relative proximity, a tuning for a receiving antenna of the medical device; and causing the receiving antenna to be tuned according to the determined tuning.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
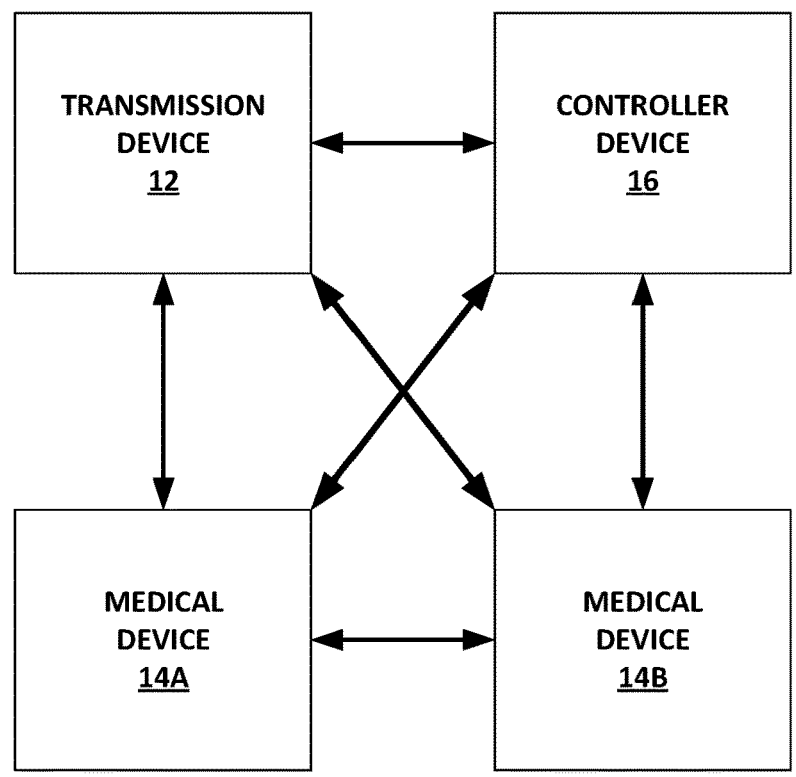
FIG. 1 is a block diagram illustrating an example system for wirelessly charging a medical device.

Various aspects of systems and techniques for wirelessly charging a wearable and/or implantable medical device are described in this disclosure. For clarity of understanding only, the techniques of this disclosure are described with respect to a continuous glucose monitor (CGM) and/or an insulin pump as exemplary medical devices, however, the techniques of this disclosure may similarly apply to wearable, implantable, or portable medical devices.

A clinician may fit a patient with one or more wearable medical devices, and/or implant the patient with one or more implantable medical devices, so as to treat a medical condition for a patient without substantially disrupting the patient's mobility or otherwise substantially interfering with the patient's lifestyle or general comfort. Wearable medical devices are also beneficial for ease of replacement. Implantable medical devices are also beneficial for ensuring continuous wear.

As one illustrative example, a diabetic patient's naturally produced insulin may not properly control the glucose level in the patient's bloodstream due to, for example, an insufficient production of insulin and/or an insulin resistance. To control the patient's glucose level, a patient may wear or be implanted with a continuous glucose monitor (CGM) to monitor the patient's glucose level and/or an insulin pump to modify the patient's glucose level. Some example medical devices such as these may include an internal rechargeable battery that provides electrical power to operate the respective devices. These medical devices are periodically removed from the patient's body in order to recharge the rechargeable batteries, during which time the medical device is typically inoperable with regard to its primary functionality in treating the patient's condition.

In accordance with the techniques of this disclosure, wearable and/or implantable medical devices, such as CGMs and insulin pumps, include a receiving antenna configured to wirelessly receive electrical power via electromagnetic radiation from an electrical-power-transmission device. The transmission device may transfer, and the receiving antenna may receive, the electrical power via far-field, microwave-spectrum electromagnetic (EM) waves, although other frequencies of the EM spectrum are likewise suitable to transfer the electrical power. Furthermore, the systems and techniques described herein are configured to manage the wireless charging of the rechargeable battery of the medical device, e.g., by monitoring one or more parameters and dynamically modifying power-transfer levels between the respective devices based at least in part on the monitored parameters. For example, in accordance with various aspects of the techniques described in this disclosure, a medical system may include a device having one or more processors (e.g., integrated computing devices) configured to determine, via any of a number of suitable mechanisms as detailed further below, a relative proximity of a medical device to the body of the patient, and in response (e.g., based on the relative proximity), determine a corresponding appropriate or suitable power-transfer level for the medical device. The processor(s) may then automatically cause the receiving antenna of the medical device to be detuned, in order to achieve or produce the determined appropriate power-transfer level.

As one illustrative example, the system (e.g., the one or more processor(s) of the system) may determine, based on received sensor data, that the medical device is currently being worn on (e.g., is currently in physical contact with) the body of the patient. In response, the system may be configured to automatically modify a tuning (e.g., "tune" or "detune," as appropriate) the receiving antenna of the medical device according to the determined power-transfer level, thereby modifying the electrical-power-transfer level between the transmission antenna of the transmission device and the receiving antenna of the medical device, in order to improve or enhance the safety and/or comfort of the patient.

More specifically, if the medical device is on or near the patient, the receiving antenna is detuned to reduce the efficiency of the charging efficiency from received electromagnetic waves in order to improve the comfort and safety of the patient, such as by maintaining a comfortable temperature of the medical device and reducing a risk of the medical device overheating while positioned on or near the patient. However, if the medical device not near the patient, the receiving antenna is tuned such that the medical device charges with greater efficiency due to the received electromagnetic waves which may, in rare cases, increase a likelihood that the medical device becomes marginally warmer during efficient charging. However, in such cases, the patient would not be proximal to the medical device to experience any change in temperature. Other various examples of intelligently managed wireless charging techniques are detailed further below.

FIG. 1 is a conceptual block diagram illustrating an example system 10 for wirelessly charging one or more medical devices, in accordance with the techniques of this disclosure. System 10 includes transmission device 12, one or more medical devices 14A, 14B (collectively, "medical devices 14" or when generally referring to a common property of either device, "medical device 14"), and, in some examples, patient controller device 16.

Figure 3:
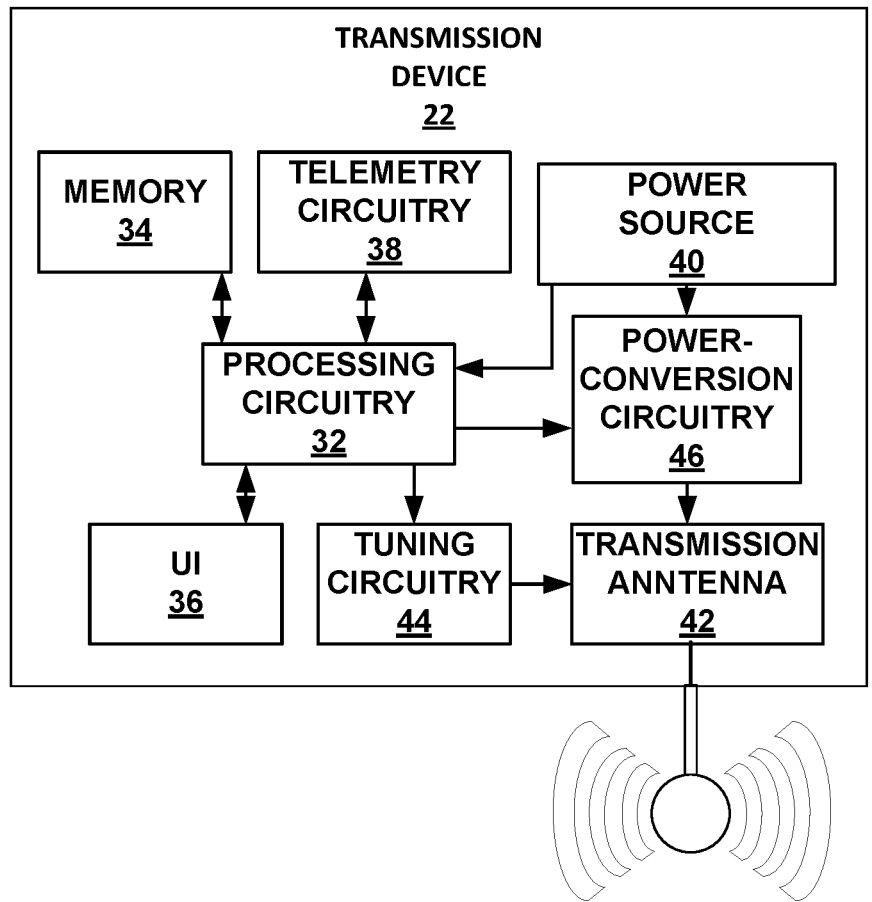
FIG. 3 is a block diagram illustrating an example of the wireless-power-transfer device of FIG. 2.

As described further below with respect to FIG. 3, transmission device 12 (e.g., a wireless-power transfer device) is configured to receive electrical power that is converted to an electromagnetic signal and broadcasted. For example, transmission device 12 may be either removably conductively coupled to an electrical power grid, such as plugged into a standard electrical outlet, or in other examples, may be permanently conductively coupled to an electrical power grid, such as fixedly integrated with the electrical wiring of a building, vehicle, or other electrically powered structure. As shown in FIG. 3 below, transmission device 12 includes at least one transmission antenna configured to receive electrical power that is converted to an electromagnetic signal and broadcasted at a particular frequency, based on the physical properties of the transmission antenna.

As one non-limiting example, transmission device 12 may include power-conversion circuitry configured to receive an electrical current and output electromagnetic waves at microwave frequencies, referred to herein as "far-field" waves. Far-field waves may typically have an effective wireless-charging range on the order of tens of meters, such as around ten to twenty meters. At this wavelength, far-field waves can propagate through non-conductive material and/or reflect off of surfaces to transmit power to medical devices 14.

Figure 4:
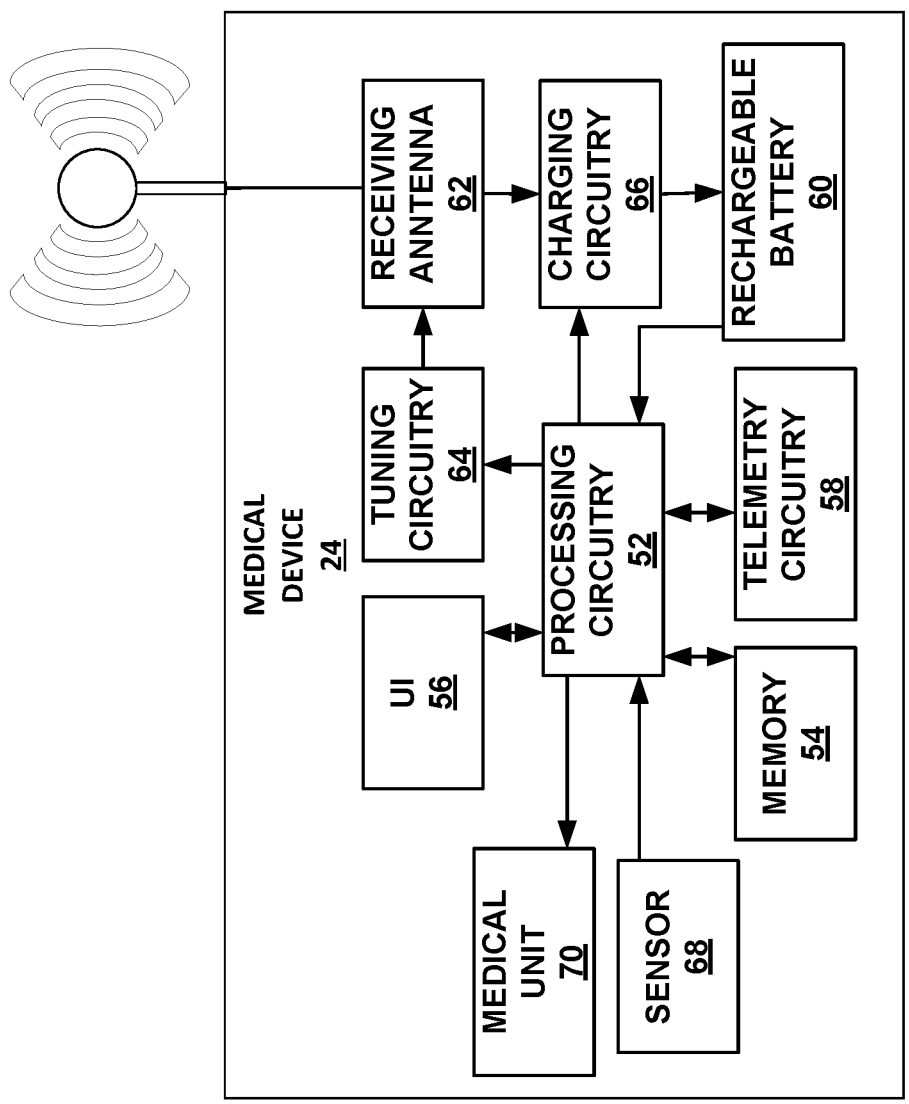
FIG. 4 is a block diagram illustrating an example of the medical device of FIG. 2.

As described further below with respect to FIG. 4, medical devices 14 include wearable, implantable, or otherwise highly portable medical instruments, each having an internal rechargeable battery and being configured to perform at least one medical function involved in the treatment of a patient condition. As shown in FIG. 4 below, medical devices 14 further include a receiving antenna configured to wirelessly receive (e.g., capable of wirelessly receiving) electrical power from transmission device 12, and corresponding circuitry configured to produce an electrical current to charge the rechargeable battery within medical device 14. For example, the receiving antenna, in concert with a resistor-inductor-capacitor (RLC) circuit may be configured to receive EM waves from transmission device 12, and convert the energy of the EM waves back into an electrical current to recharge the rechargeable battery of the medical device.

As described further below with respect to FIG. 5, patient controller device 16 (also referred to herein as "patient device 16" and "controller device 16") may be configured to enable a user to manually control a functionality of medical devices 14 and/or transmission device 12. Controller device 16 includes a user interface (UI) (e.g., user input and output components) configured to enable a user (such as a patient or clinician) to manually activate, deactivate, or modify one or more of the wireless-power transmission of transmission device 12, the wireless recharging of medical devices 14, and/or the medical-treatment functionalities of medical devices 14.

As indicated by the double-headed arrows shown in FIG. 1, any or all of transmission device 12, medical devices 14, and controller device 16 may be in data communication with one another. For example, all of the indicated devices may include wired or wireless data-transmission-and-receiving capabilities (e.g., through a wireless link connection, like Bluetooth™, Bluetooth Low-Energy (BLE), Wi-Fi®, or other personal area network protocol and/or wireless protocol) and processing circuitry configured to process telemetry data or other data from any of the other devices of system 10.

In accordance with the techniques of this disclosure, system 10 includes at least one computing device having one or more processors (e.g., processors of transmission device 12, medical devices 14, and/or controller device 16, referred to collectively herein as "processors of system 10") configured to automatically manage the wireless recharging of medical devices 14 in order to improve patient comfort and safety, to conserve energy resources, and/or to prolong a useful lifespan of components of system 10, among other benefits and practical applications as described herein. As one non-limiting, illustrative example, any or all of the devices of system 10 may include computing capabilities, such as one or more processors, configured to determine, via any of a number of suitable mechanisms as detailed further below, a relative proximity of medical device 14 to the body of a patient, and in response (e.g., based on the relative proximity), determine a corresponding appropriate or suitable power-transfer level to enhance patient comfort and safety. The processor(s) may further determine a tuning of either or both of the transmission antenna of transmission device 12 or the receiving antenna of medical device 14 that corresponds to the determined power-transfer level, and then automatically adjust or modify (e.g., tune or detune) the antenna(s) as appropriate.

For example, the one or more of the processors of system 10 may determine, such as based on received sensor data, user input or other data, that medical device 14 is currently in physical contact with (e.g., is currently being worn on or implanted within) the body of a patient. In response, the one or more processors of system 10 may be configured to automatically detune the transmission antenna of transmission device 12 and/or the receiving antenna of medical device 14 by, for example, adjusting the inductor of an RLC circuit conductively coupled to the respective antenna, thereby reducing the electrical-power-transfer level between the transmission antenna of transmission device 12 and the receiving antenna of the medical device 14. In doing so, system 10 may reduce a likelihood that an excess amount of electrical power that would otherwise have been received by medical device 14 would produce additional waste heat that could potentially cause discomfort to the patient when medical device 14 is worn by or implanted within the patient. In other such examples, such as when medical device 14 includes an insulin pump that stores a reservoir of liquid insulin, system 10 may reduce this waste heat so as to preserve the efficacy and/or potentially extend the shelf-life of the supply of insulin.

As another example, the one or more processors of system 10 may determine, such as based on received sensor data, user input, or other data, that medical device 14 is not currently in physical contact with (e.g., is not currently worn by or implanted within), and is not proximate to (e.g., is not within a threshold distance of) the body of the patient. In response, the one or more processors of system 10 may automatically deactivate transmission device 12 in order to conserve electrical power, or in other examples, by automatically tuning or detuning the transmission antenna and/or receiving antenna to increase the power-transfer level since medical device 14 is not proximate to the patient.

As used herein, the "threshold" distance between the medical device 14 and the body of the patient 28 may depend on several factors, consistent with the principle that a closer (e.g., below-threshold) distance corresponds to a reduction in power-transfer levels (e.g., power-transfer efficiency), and conversely, that a farther (e.g., above-threshold distance) corresponds to an increase in power-transfer levels (e.g., power transfer efficiency).

A first example of a threshold distance between medical device 14 and patient 28 may include a "minimum" threshold distance. For instance, a "minimum" threshold distance may correspond to a width or thickness of an exterior housing of medical device 14, such that a receiving antenna of medical device 14 is in physical contact with an interior surface of the housing, and the body of patient 28 is in physical contact with the exterior surface of the housing. In such examples, this minimum threshold distance is configured to indicate a binary determination of whether the medical device 14 is currently being worn by (e.g., in contact with the body of) the patient 28. In such cases (e.g., when device 14 is worn by patient 28 or is within another similar threshold distance of patient 28), system 10 may determine (e.g., select) and control a corresponding power-transfer efficiency such that the rechargeable battery of medical device 14 recharges at a rate at which heat generation is minimal, e.g., is not directly observable or detectable by patient 28. In many cases, the maximum charge current (e.g., the fastest rate at which the battery may be recharged without producing excess waste heat) is dependent upon the performance of the rechargeable battery, among other factors.

A second example of a threshold distance between medical device 14 and patient 28 may include a "maximum" threshold distance. For instance, as described further below with respect to FIGS. 9A-9C, a relative proximity of patient 28 to medical device 14 may cause the resonance frequency of the receiving antenna to shift to a characteristic frequency fc. In such examples, the relative proximity of patient 28 to medical device 14 may inherently cause a "mismatch" between an actual broadcast frequency of the wireless power and an "ideal" broadcast frequency (e.g., the characteristic frequency of the receiving antenna), resulting in a reduced power-transfer efficiency. In other words, the greater the distance between medical device 14, the greater the power-transfer efficiency between the transmission antenna and the receiving antenna, up to a certain distance at which further increases in power-transfer efficiency are negligible. In some such examples, a "maximum" threshold distance between medical device 14 and patient 28 may correspond to the distance at which the power-transfer efficiency between the transmission device 12 and the medical device 14 is sufficiently high that an amount of received power is equal to (or greater than) an amount of electrical power required to operate processing circuitry and/or other functionality of medical device 14. At below-threshold distances (e.g., at distances between medical device 14 and patient 28 at which the received power is less than the required processing power), system 10 may be configured to automatically cause the processing circuitry (or other circuitry) of medical device 14 to a low-power "discovery" mode to enable more of the (reduced) received power to be directed toward recharging the internal battery.

In some examples, the one or more processors of system 10 may be configured to automatically tune the transmission antenna of transmission device 12 and/or the receiving antenna of medical device 14, and/or activate or deactivate charging circuitry within medical device 14, in order to maintain a predetermined level of power (e.g., energy capacity) within the rechargeable battery. For example, system 10 may be configured to maintain at least a certain minimum threshold of energy capacity, or in other words, maintain a preferred range of energy capacities, within the rechargeable battery when the medical device 14 is not worn by the patient (e.g., when medical device 14 is in storage or is otherwise not in use), which has been found to substantially prolong a remaining useful lifespan (e.g., a remaining number of recharge cycles) of rechargeable batteries. As one non-limiting, illustrative example, rechargeable batteries maintained with at least about 30% battery capacity (e.g., from about 15% to about 45% battery capacity) while not in use have been found to have substantially prolonged useful lifespans, as compared to some rechargeable batteries that have been allowed to naturally discharge down to 0% capacity while not in use. However, the particular preferred or "optimal" minimum battery capacity is highly dependent on the physical properties of each rechargeable battery.

Accordingly, when the battery capacity falls below the predetermined minimum threshold, the one or more processors of system 10 configure medical device(s) 14 to be in a state in which medical device(s) 14 can be recharged or more-efficiently recharged (e.g., by tuning the receiving antenna and/or re-activating a recharging system, such as charging circuitry 66 of FIG. 4), in order to restore (e.g., maintain) the minimum threshold of battery capacity. Similarly, when the battery capacity reaches a predetermined maximum threshold (e.g., at full battery capacity or another predetermined maximum battery capacity level), the one or more processors of system 10 configure medical device(s) 14 to be in a in a state in which medical device(s) cannot be efficiently recharged or cannot be recharged at all (e.g., detunes the receiving antenna and/or deactivates the recharging system). In some examples, system 10 may be configured to maintain the minimum level of battery capacity in response to determining that medical device 14 is not currently worn by the patient (e.g., is not within a threshold distance of the body of the patient), according to one or more of the techniques described herein. In other examples, system 10 may be configured to maintain the minimum level of battery capacity regardless of whether a determination of patient-body proximity has been made.

In some examples, system 10 may further be configured to determine a present discharge rate (e.g., either the load-discharge rate resulting from a current usage of medical device 14, or alternatively, the natural self-discharge rate while medical device 14 is not in use) of the rechargeable battery of medical device 14. In response, system 10 may be configured to automatically tune (or detune, as appropriate) the antennae of transmission device 12 and/or medical device 14 such that the electrical-power-transfer level (e.g., power-transfer rate) between the transmission device 12 and medical device 14 is approximately equal to (e.g., is within a threshold tolerance of) the discharge rate of the rechargeable battery of medical device 14, thereby maintaining a particular predetermined level of battery capacity within the rechargeable battery (as compared to the previous example, in which system 10 allows the battery capacity to fluctuate within a predetermined range of battery-capacity levels).

In this way, system 10 may simultaneously or separately achieve at least three different benefits or practical applications of system 10 by (1) conserving electrical power (e.g., drawing and transmitting only a precisely required amount of required energy to maintain the predetermined capacity level), (2) enhancing patient comfort and safety (e.g., reducing excess "wasted" power that could otherwise be converted to waste heat), and (3) prolonging the useful lifespan of the rechargeable battery (e.g., maintaining a predetermined "optimal" level of battery capacity). The example techniques should not be considered as requiring the example benefits described above, or be considered as limited to providing the example benefits described above.

Figure 2:
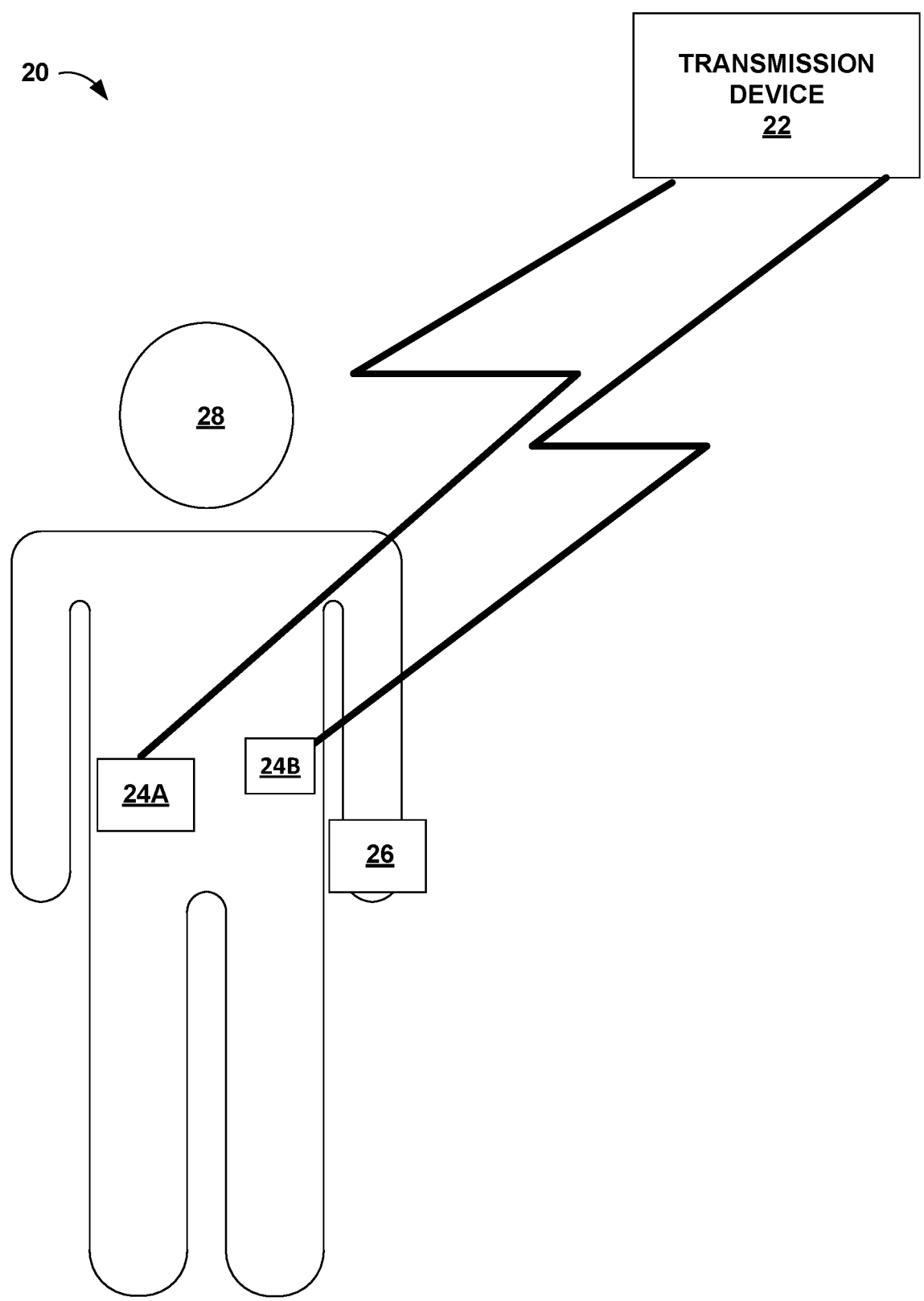
FIG. 2 is a conceptual diagram illustrating an example of the medical system of FIG. 1.

FIG. 2 is a block diagram illustrating an example system 20, which is an example of system 10 of FIG. 1, for wirelessly charging a medical device 24 (FIG. 4) in accordance with one or more examples described in this disclosure. System 20 includes a wireless-power transmission device 22 (e.g., transmission device 12 of FIG. 1), a first medical device 24A (also referred to herein as "glucose sensor 24A," "sensor 24A," "monitor 24A," or CGM 24A," which is an example of medical device 14A of FIG. 1), a second medical device 24B (also referred to herein as "insulin pump 24B," which is an example of medical device 14B of FIG. 1), and a patient device 26 (which is an example of controller device 16 of FIG. 1). Medical devices 24A, 24B (collectively, "devices 24" or when generally referring to a common property of each, "medical device 24") of system 20 are configured to be used with, on, by, or on behalf of, a user, such as patient 28, in order to treat a medical condition of patient 28. Although FIG. 2 illustrates two medical devices 24, in some examples of system 20, there may only one medical device 24, or in other examples, there may be more than two medical devices 24. In some examples, system 20 may be referred to as a continuous glucose monitoring (CGM) system or a closed-loop system. Although FIG. 2 depicts medical devices 24 being worn on an abdomen of patient 28, these particular locations of medical devices 24 are provided for ease of illustration only. Medical device(s) 24 may be worn elsewhere, such as on an arm of patient 28, or in some examples, implanted within the body of patient 28.

Patient 28 may be diabetic (e.g., Type 1 diabetic or Type 2 diabetic), and therefore, the glucose level in patient 28 may be uncontrolled without delivery of supplemental insulin. For example, patient 28 may not produce sufficient insulin to control the patient's glucose level, or the amount of insulin that patient 28 produces may not be sufficient, such as due to an insulin resistance that patient 28 may have developed.

Glucose sensor 24A may be coupled to patient 28 to measure a glucose level in patient 28. To receive supplemental insulin, patient 28 may also carry or wear insulin pump 24B for delivery of insulin into patient 28. Insulin pump 24B may include an infusion set that connects to the skin of patient 28, and a cannula to deliver insulin into patient 28. Sensor 24A and insulin pump 24B may together form an insulin-pump system. One example of the insulin pump system is the MINIMED™ 670G INSULIN PUMP SYSTEM by Medtronic plc of Dublin, Ireland. However, other examples of insulin-pump systems may be used and the example techniques should not be considered limited to the MINIMED™ 670G INSULIN PUMP SYSTEM.

Insulin pump 24B may be a relatively small device that patient 28 can place in different locations. For instance, patient 28 may clip insulin pump 24B to the waistband of pants worn by patient 28. In some examples, to be discreet, patient 28 may place insulin pump 24B in a pocket. In general, insulin pump 24B can be worn in various places (or implanted on patient 28) and patient 28 may place insulin pump 24B in a location based on the particular clothes patient 28 is wearing.

To deliver insulin, insulin pump 24B includes one or more reservoirs (e.g., two reservoirs). A reservoir may be a plastic cartridge having a capacity to hold a certain number of units of insulin (e.g., up to 300 units of insulin) and is locked into insulin pump 24B. Insulin pump 24B is a battery-powered device that is powered by one or more rechargeable batteries.

In some examples, insulin pump 24B includes tubing, sometimes called a catheter, that connects on a first end to the reservoir within insulin pump 24B, and connects on a second end to the infusion set of insulin pump 24B. The tubing may carry the insulin from the reservoir of insulin pump 24B to the body of patient 28. The tubing may be flexible, allowing for looping or bends to reduce concern of the tubing becoming detached from insulin pump 24B or concern of the tubing breaking.

The infusion set of insulin pump 24B may include a thin cannula that patient 28 inserts into a layer of fat under the skin (e.g., subcutaneous connection). The infusion set may rest on or near the abdomen of patient 28. The insulin travels from the reservoir of insulin pump 24B, through the tubing, through the cannula in the infusion set, and into the body of patient 28. In some examples, patient 28 may utilize an infusion-set-insertion device. Patient 28 may place the infusion set into the infusion-set-insertion device, and with a push of a button on the infusion-set-insertion device, the infusion-set-insertion device may insert the cannula of the infusion set into the layer of fat of patient 28, and the infusion set may rest on top of the skin of the patient with the cannula inserted into the layer of fat of patient 28.

Glucose sensor 24A may include a sensor that is inserted under the skin of patient 28, such as at or near the abdomen of patient 28 or in the arm of patient 28 (e.g., subcutaneous connection). The sensor of sensor 24B may be configured to measure the interstitial glucose level, which is the glucose found in the fluid between the cells of patient 28 (which also may be referred to as the "sensor glucose" ("SG") level, as distinguished from the "blood glucose" ("BG") level, given that the SG measures the glucose in the interstitial fluid between cells, whereas the BG measures glucose in the blood). Sensor 24A may be configured to continuously or periodically sample the patient's glucose level and rate of change of the glucose level over time.

In one or more examples, glucose sensor 24A and insulin pump 24B may together form a closed-loop therapy-delivery system. For example, patient 28 may set a target glucose level, usually measured in units of "milligrams per deciliter," for insulin pump 24B. Insulin pump 24B may receive an indication of a measurement of a "current" glucose level from sensor 24A, and in response, may increase or decrease (as appropriate) the amount of insulin delivered to patient 28. For example, if the current glucose level is higher than the target glucose level, insulin pump 24A may increase the amount of delivered insulin. If the current glucose level is lower than the target glucose level, insulin pump 24B may temporarily reduce, or in some examples, cease (e.g., refrain from) delivery of the insulin to the body of patient 28. Insulin pump 24B may be considered to be an example of an automated-insulin-delivery (AID) device. Other examples of AID devices may be possible, and the techniques described in this disclosure may be applicable to other AID devices.

For example, insulin pump 24B and sensor 24A may be configured to operate together to mimic some of the ways in which a healthy pancreas works. Insulin pump 24B may be configured to deliver basal insulin, which is a small amount of insulin released continuously throughout the day. There may be times when glucose levels increase, such as due to eating or some other activity that patient 28 undertakes such as sleep, exercise, etc. Insulin pump 24B may be configured to deliver bolus insulin on demand in association with food intake or to correct an undesirably high glucose level in the bloodstream. In one or more examples, if the glucose level rises above a target level, then insulin pump 24B may increase the bolus insulin to address the increase in glucose level. Insulin pump 24B may be configured to compute basal and bolus insulin delivery, and deliver the basal and bolus insulin accordingly. For instance, insulin pump 24B may determine the amount of basal insulin to deliver continuously, and then determine the amount of bolus insulin to deliver to reduce glucose level in response to an increase in glucose level due to eating (or other ingestion of carbohydrates) or some other event.

Accordingly, in some examples, sensor 24A may sample glucose level and rate of change in glucose level over time. Sensor 24A may output the glucose level to insulin pump 24B (e.g., through a wireless link connection, like Bluetooth™, BLE, Wi-Fi®, or other personal area network protocol and/or wireless protocol). Insulin pump 24B may compare the glucose level to a target glucose range, or in other words, prescribed glucose range (e.g., as set by patient 28 or a clinician), and adjust the insulin dosage based on the comparison.

As described above, patient 28 or a clinician may set a prescribed (e.g., target) glucose range for insulin pump 24B. There may be various ways in which patient 28 or the clinician may set the prescribed glucose range on insulin pump 24B. As one example, patient 28 or the clinician may utilize patient device 26 to communicate with insulin pump 24B. Examples of patient device 26 include mobile computing devices, such as smartphones or tablet computers, laptop computers, and the like. In some examples, patient device 26 may be a customized programmer or controller device for insulin pump 24B. Although FIG. 1 illustrates one patient device 26, in some examples, there may be a plurality of patient devices. For instance, system 20 may include a mobile device and a distinct controller device, each of which are examples of patient device 26. For ease of description only, the example techniques are described with respect to patient device 26, with the understanding that patient device 26 may be one or more patient devices.

In some examples, patient device 26 may include a wearable device, such as (but not limited to) a smartwatch or a fitness tracker, either of which may, in some examples, be configured to be worn on a patient's wrist or arm, e.g., as a wrist watch or band. In one or more examples, patient device 26 includes one or more accelerometers (e.g., a six-axis accelerometer). Patient device 26 may be configured to determine one or more movement characteristics of patient 28. Examples of the one or more movement characteristics include values relating to frequency, amplitude, trajectory, position, velocity, acceleration and/or pattern of movement currently or over time. The frequency of movement of the patient's arm may refer to how many times patient 28 repeated a movement within a certain time (e.g., such as frequency of movement back and forth between two positions).

Patient device 26 may also be configured to interface with glucose sensor 24A. As one example, patient device 26 may receive information (e.g., glucose level or rate of change of glucose level) directly from sensor 24A (e.g., through the wireless link). As another example, patient device 26 may receive information from sensor 24A through insulin pump 24B, where insulin pump 24B relays the information between patient device 26 and sensor 24A.

In one or more examples, patient device 26 may display a user interface (UI) with which patient 28 or a clinician may control insulin pump 24B. For example, patient device 26 may display a screen that allows patient 28 or the clinician to enter the prescribed or target glucose range. As another example, patient device 26 may display a screen that outputs the current glucose level. In some examples, patient device 26 may output notifications (or, in other words, alerts) to patient 28, such as notifications if the glucose level is too high or too low, as well as notifications regarding any action that patient 28 needs to take. For example, if the batteries of insulin pump 24B are low on charge, then insulin pump 24B may output a "low battery" indication to patient device 26, and patient device 26 may in turn output a notification to patient 28 to manually recharge the batteries (e.g., to connect the batteries to a recharging device), or additionally or alternatively, to enable a wireless recharging mode for insulin pump 24B.

Controlling insulin pump 24B through patient device 26 is merely one example, and should not be considered limiting. For example, insulin pump 24B may include a UI (e.g., push-buttons) that allow patient 28 or the clinician to set the various prescribed glucose ranges to be provided by insulin pump 24B. Also, in some examples, insulin pump 24B itself, or in addition to patient device 26, may be configured to output notifications to patient 28. For instance, if the glucose level is too high or too low, insulin pump 24B may output an audible or haptic output. As another example, if the battery is low, then insulin pump 24B may output a "low battery" indication on a display (e.g., user interface 56 of FIG. 4) of insulin pump 24B, and/or output a notification to manually recharge the battery (e.g., to connect the battery to a recharging device), or additionally or alternatively, to enable a wireless recharging mode for insulin pump 24B.

Transmission device 22 is configured to receive electrical power that is converted to an electromagnetic signal and broadcasted. For example, transmission device 22 may be removably conductively coupled to an electrical power grid, such as plugged into a standard electrical outlet, or in other examples, may be permanently conductively coupled to an electrical power grid, such as fixedly integrated with the electrical wiring of a building, vehicle, or other electrically powered structure. As shown in FIG. 3 below, transmission device 22 includes at least one transmission antenna configured to convert an electrical current into EM waves of a particular frequency based on the physical properties of power-conversion circuitry (e.g., coupled to or integral with the transmission antenna) of transmission device 22. As one non-limiting example, transmission device 22 may include circuitry configured to receive an electrical current and output electromagnetic waves at far-field, microwave frequencies.

As detailed further below, any or all of transmission device 22, glucose sensor 24A, insulin pump 24B, and patient device 26 may include one or more processors (e.g., processing circuitry) configured to perform the techniques of this disclosure. One or more processors may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors may include arithmetic logic units (ALUs), elementary function units (EFUs), digital circuits, analog circuits, and/or programmable cores, formed from programmable circuits. In examples where the operations of one or more processors are performed using software executed by the programmable circuits, memory (e.g., on the servers) accessible by one or more processors may store the object code of the software that one or more processors receive and execute. In some examples, one or more processors may share data or resources for performing computations, and may be part of computing servers, web servers, database servers, and the like.

One or more processors, as well as other processing circuitry described herein, can include any one or more microprocessors, digital signal processors (DSPs), application-specific integrated circuits (ASICs), field programmable gate arrays (FPGAs), or any other equivalent integrated or discrete logic circuitry, as well as any combinations of such components. The functions attributed one or more processors, as well as other processing circuitry described herein, may be embodied as hardware, firmware, software or any combination thereof.

In accordance with the techniques of this disclosure, system 20 (e.g., one or more processors integrated within any of the various devices of system 20) is configured to automatically manage the wireless recharging of the rechargeable batteries within a medical device 24 (FIG. 4), such as, glucose sensor 24A and/or insulin pump 24B, in order to improve patient comfort and safety, to conserve energy resources, and/or to prolong a useful lifespan of the rechargeable batteries.

As one non-limiting, illustrative example, one or more processors of system 20 are configured to sense, detect, monitor, or otherwise determine a relative proximity of glucose sensor 24A and/or insulin pump 24B to the body of patient 28, and in response (e.g., based on the determined relative proximity), determine a corresponding appropriate or suitable wireless-power-transfer level (e.g., power-transfer rate or power-transfer efficiency), such as to enhance the comfort and/or safety of patient 28. The processor(s) may then automatically adjust or modify (e.g., tune or detune, as appropriate) the transmission antenna of transmission device 22 and/or the receiving antenna of the respective medical device 24 in order to achieve or produce the determined appropriate power-transfer level. For example, either of medical devices 24 may include a sensor, such as a flex sensor, an impedance sensor, or other suitable detection mechanism, configured to produce sensor data indicative of whether medical device(s) 24 are currently in physical contact with (e.g., currently being worn on or implanted within) the body of patient 28. In response to receiving the sensor data, the one or more processors of system 20 may be configured to determine a corresponding suitable power-transfer level and automatically "de-tune" the receiving antennae of devices 22, 24, for example, by causing tuning circuitry to adjust or modify an inductor of an RLC circuit coupled to the respective antenna. According to this example implementation, tuning or detuning the antenna in this way (e.g., via an inductor of an RLC circuit) includes modifying the resonant frequency of the antenna, thereby adjusting or modifying the particular frequency band of the EM spectrum that is not filtered or blocked from the antenna by the RLC circuit.

In some example scenarios, one or more of the processors of system 20 may be configured to automatically tune or detune the resonant frequency of the receiving antenna of medical device 24 without modifying the broadcast frequency of wireless power from transmission device 22, or in other examples, may modify the broadcast frequency of transmission device 22 without tuning or detuning the resonant frequency of the receiving antenna of medical device 24, thereby modifying (e.g., increasing or decreasing) the electrical-power-transfer level between transmission device 22 and medical device 24. For example, in response to determining that medical device 24 is proximate to (e.g., in physical contact with or within a threshold distance of) the body of patient 28, system 20 may increase a difference between the broadcast frequency of transmission device 22 and the "characteristic" frequency of the receiving antenna 62. For example, the one or more processors may be configured to tune or detune the receiving antenna 62 up to a "cutoff" frequency, beyond which the medical device 24 will wirelessly receive less than a minimal or negligible amount of power.

Because the "characteristic" resonant frequency of receiving antenna 62 is at least partially determined by (e.g., is dependent on) the relative proximity of the body of patient 28, the frequency difference (e.g., the bandwidth) between the resonant frequency of receiving antenna 62 and the "cutoff" frequency (e.g., the highest or lowest "tunable" frequency of receiving antenna 62) must be large enough to accommodate the potential shift in the characteristic frequency caused by the relative proximity of the patient's body. Some non-limiting examples of these frequency ranges include ultra-high frequencies (e.g., about 300 MHz to about 3 GHz) to super-high frequencies (e.g., about 3 GHz to about 30 GHz). These super-high frequency ranges may be preferable due to the relatively smaller size of receiving antenna 62 (e.g., in order to fit within medical device 24).

In this way, system 20 may reduce a likelihood that an amount of electrical power that would otherwise have been transferred to (e.g., received by) medical device 24 would produce excess waste heat that could potentially cause discomfort to the patient when medical device 24 is worn by the patient. In other examples, such as in response to determining that medical device 24 is not proximate to (e.g., is not in physical contact with or is not within a threshold distance of) the body of patient 28, system 20 may decrease a difference between the broadcast frequency of transmission device 22 and the resonant frequency of the receiving antenna. In this way, system 20 may cause the rechargeable battery of medical device 24 to charge more quickly (e.g., more efficiently). In other examples, such as in response to determining that medical device 24 is not proximate to the body of patient 28 and determining that the rechargeable battery is at full capacity, the one or more processors of system 20 may be configured to automatically deactivate the transmission of wireless electrical power from transmission device 22 in order to conserve electrical power.

In some examples, the one or more processors of system 20 may be configured to automatically tune the transmission antenna of transmission device 22 or the receiving antenna of medical device 24, and/or dynamically activate and deactivate power-conversion circuitry within transmission device 22 and/or charging circuitry within medical device 24, in order to maintain a certain predetermined level of power (e.g., battery capacity) within the rechargeable battery of medical device 24. For example, system 20 may be configured to maintain a certain minimum threshold of battery capacity (e.g., a predetermined range of battery capacities) within the rechargeable battery, such as when the medical device 24 is not worn by the patient (e.g., when medical device 24 is in storage or is otherwise not in use), in order to substantially prolong a remaining useful lifespan of the rechargeable battery. For example, the one or more processors of system 20 configure medical device 24 to be in a state in which medical device 24 can be recharged or more-efficiently recharged (e.g., by tuning the receiving antenna and/or re-activating a recharging system, such as charging circuitry 66 of FIG. 4) when the battery capacity falls below the predetermined minimum threshold in order to maintain the minimum threshold of battery capacity. Similarly, the one or more processors of system 20 configure medical device 24 to be in a state in which medical device 24 may not be efficiently recharged, or may not be recharged at all, when the battery capacity reaches a predetermined maximum threshold (e.g., full capacity or another predetermined capacity level).

In some examples, system 20 may be configured to accurately determine a present discharge rate (e.g., either the load-discharge rate caused by a usage of medical device 24, or the natural self-discharge rate while medical device 24 is not in use) of the rechargeable battery of medical device 24, and in response, automatically tune transmission device 22 and/or medical device 24 such that the electrical-power-transfer level (e.g., power-transfer rate) between the transmission antenna of transmission device 22 and the receiving antenna of medical device 24 is approximately equal to (e.g., is within a threshold tolerance of) the present discharge rate of the rechargeable battery of medical device 24. In this way, system 20 may conserve electrical power (e.g., by drawing and wirelessly transmitting only a precise amount of required energy), enhance patient comfort and safety (e.g., by reducing excess received power that could otherwise be converted to waste heat), and/or prolonging the useful lifespan of the rechargeable battery.

FIG. 3 is a block diagram illustrating some example components of transmission device 22 of FIG. 2, which is an example of transmission device 12 of FIG. 1, in accordance with one or more examples described in this disclosure. As described above, transmission device 22 is configured to receive electrical power that is converted to an electromagnetic signal and broadcasted from transmission antenna 42. As shown in FIG. 3, transmission device 22 includes processing circuitry 32, memory 34, user interface (UI) 36, telemetry circuitry 38, power source 40, transmission antenna 42, tuning circuitry 44, and power-conversion circuitry 46. Memory 34 may store program instructions that, when executed by processing circuitry 32, cause processing circuitry 32 to provide the functionality ascribed to transmission device 22 throughout this disclosure.

In some examples, memory 34 of transmission device 22 may store a plurality of parameters, such as specific (e.g., predetermined) levels (e.g., amplitudes) of wireless power to transmit, specific frequencies of the EM spectrum to transmit, etc. Processing circuitry 32 may retrieve the parameters stored in memory 34, such as in response to receiving a command from patient device 26 via telemetry circuitry 38, to cause power-conversion circuitry 46 to generate and output, via transmission antenna 42, an EM signal according to the parameters (e.g., having the desired amplitude and frequency). In other words, medical device(s) 24 may inform patient device 26 of a low battery capacity, and in response, patient device 26 will command transmission device 22 to output electrical power according to the parameters retrieved from memory 34.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

UI 36 may include a button or keypad, lights, a speaker for voice commands, and a display, such as a liquid crystal (LCD) a light emitting diode (LED) display, an organic LED (OLED) display, etc. In some examples the display may be a presence-sensitive display. As discussed in this disclosure, processing circuitry 32 may present and receive information relating to electrical-power-transmission levels via UI 36. For example, processing circuitry 32 may receive user input via user interface 36. The user input may be entered, for example, by pressing a button on a keypad, entering text, or selecting an icon from a touch screen. The user input may be information indicative of a desired wireless-power-transfer amplitude or frequency.

Telemetry circuitry 38 includes any suitable hardware, firmware, software or any combination thereof for communicating with another device, such as glucose sensor 24A (FIG. 2), insulin pump 24B, and patient device 26. Telemetry circuitry 38 may receive communication with the aid of an antenna, which may be internal and/or external to transmission device 22, and which may be the same as, or different from, transmission antenna 42. Telemetry circuitry 38 may be configured to communicate with another computing device via wireless communication techniques, or direct communication through a wired connection. Examples of local wireless communication techniques that may be employed to facilitate communication between transmission device 22 and another computing device include RF communication according to IEEE 802.11 or Bluetooth specification sets, infrared communication, e.g., according to an IrDA standard, or other standard or proprietary telemetry protocols.

Power source 40 delivers both operating power to the components of transmission device 22, as well as an electrical power supply delivered to power-conversion circuitry 46 to convert to a wireless EM signal broadcast by transmission antenna 42. In some examples, power source 40 may include an electrical cord and plug for removable connection to a power outlet. In other examples, power source 40 may include a permanent wired connection to a power grid or other virtually continuous power source, such as when transmission device 22 is integrated within a building or vehicle.

According to the techniques of this disclosure, as in one or more of the example scenarios described above with respect to FIGS. 1 and 2, processing circuitry 32 is configured to cause tuning circuitry 44 to modify a frequency of the EM signal broadcast by transmission antenna 42, such as by modifying an inductor of an RLC circuit or another physical property of an electronic circuit of transmission device 22. For example, processing circuitry 32 is configured to cause tuning circuitry 44 to "tune" transmission antenna 42 to broadcast far-field EM waves, which may include microwave frequencies from about 1 GHz to about 1000 GHz, corresponding to wavelengths of about 30 cm to about 0.03 cm. Similarly, processing circuitry 32 is configured to cause tuning circuitry 44 to "detune" transmission antenna 42 to broadcast lower-frequency EM waves, such as radio waves.

Similarly, processing circuitry 32 is configured to cause power-conversion circuitry 46 to enable or disable a broadcast of an EM signal from transmission antenna 42, such as by opening or closing a switch of power-conversion circuitry 46. In some examples, power-conversion circuitry may include a transformer or other electronic components configured to modify a voltage or current of the power supply from power source 40 before converting the power supply to a broadcast EM signal.

In some examples, processing circuitry 32 of transmission device 22 is configured to determine (e.g., calculate) a relative location of medical device 24, or more specifically, a relative location of receiving antenna 62 (FIG. 4) of either or both of medical devices 24. For instance transmission antenna 42 of transmission device 22 may include a 3-D antenna array configured to enable transmission device 22 to determine the relative location and/or the broadcast strength of receiving antenna 62 receiver broadcast strength. For example, transmission device 22 may be configured to determine the relative location of receiving antenna 62, and in some examples, a shortest "clear" (e.g., obstacle-free) path between transmission device 22 and medical device 24, based on a minimal phase shift (e.g., phase delay) and based on a highest received broadcast strength received by the 3-D antenna array in transmission device 22. The determined "shortest" path may include, for instance, a path that naturally avoids obstacles that would otherwise obstruct or attenuate a wireless signal. In some examples, this shortest path may be non-linear in nature, e.g., may include one or more reflections of the wireless signal in order to avoid obstacles (e.g., metal, the body of patient 28, etc.) located along a more-direct route to the receiving antenna 62. After determining the shortest clear path to receiving antenna 62, transmission device 22 may use the 3-D antenna array to wirelessly "beam" the electromagnetic energy back to the receiving antenna 62 along the determined path. The shortest path determined would naturally avoid obstacles such as human body, metal, etc.

A set of illustrative scenarios involving the functionality of the components of transmission device 22 follows. As a first example, processing circuitry 32, via telemetry circuitry 38, receives an indication that a medical device 24 (e.g., either of medical device 24A or medical device 24B) is at low battery capacity, and also that medical device 24 is not proximal to patient 28 (FIG. 2). One example of this scenario is while medical device 24 is located in storage, such that the battery may be allowed to cyclically drain, and then be efficiently recharged, while remaining within a predetermined range of minimum-to-maximum preferred battery capacities. In such cases, processing circuitry 32 causes tuning circuitry 44 to tune transmission antenna 42 to a resonant frequency of receiving antenna 62 (FIG. 4) of medical device 24, because any temperature change resulting from the power transfer will not affect patient 28.

Processing circuitry 32 also causes power-conversion circuitry 46 to enable the broadcast of an EM signal at the resonant frequency.

As a second example, processing circuitry 32, via telemetry circuitry 38, receives an indication that a medical device 24 is at low battery capacity, and also that medical device 24 is proximal to patient 28. In such cases, processing circuitry 32 causes tuning circuitry 44 to detune transmission antenna 42 to a lower "detuned" frequency than the resonant frequency of receiving antenna 62 of medical device 24, and also causes power-conversion circuitry 46 to enable the broadcast of an EM signal at the "detuned" frequency. In such examples, patient comfort and safety is ensured, while simultaneously reducing or preventing disruptions to the patient's therapy due to an excessively low-capacity (e.g., "dead") battery. However, in some such cases, the "detuned" recharge rate of the battery of medical device 24 may be lower than the battery's discharge rate resulting from use of the primary functionality of medical device 24. In some such examples, the battery of medical device 24 may continue to discharge, albeit at a slower rate than if the wireless power transfer was disabled entirely. Upon reaching a second predetermined "low" battery capacity, patient 28 may receive a notification (e.g., from patient device 28) that medical device 24 needs to be removed from the patient's body and efficiently recharged.

As a third example, processing circuitry 32, via telemetry circuitry 38, receives an indication that a medical device 24 is at a maximum (e.g., full or other predetermined) battery capacity, and also that medical device 24 is proximal to patient 28. In such cases, processing circuitry 32 causes tuning circuitry 44 to detune transmission antenna 42 to a lower, detuned frequency (if antenna 42 is not already at the detuned frequency), and also causes power-conversion circuitry 46 to disable the broadcast of an EM signal at the detuned frequency.

As a fourth example, processing circuitry 32, via telemetry circuitry 38, receives an indication that medical device 24 is at a maximum (e.g., full or other predetermined) battery capacity, and also that medical device 24 is not proximal to patient 28. In such cases, processing circuitry 32 causes tuning circuitry 44 to tune transmission antenna 42 to a resonant frequency of receiving antenna 62 (FIG. 4) of medical device 24 (if antenna 42 is not already at the resonant frequency), and also causes power-conversion circuitry 46 to disable the broadcast of an EM signal. In an alternative example, in response to receiving the indication, processing circuitry 32 causes tuning circuitry 44 to detune transmission antenna 42 to a known "trickle" frequency of receiving antenna 62 of medical device 24, or in other words, a frequency that results in a power-transfer efficiency between transmission antenna 42 and receiving antenna 62 that recharges the battery of medical device 24 at a rate that is equal to the natural (e.g., "trickle") discharge rate of the battery while medical device 24 is not in use. In such examples, processing circuitry 32 also causes power-conversion circuitry 46 to enable the broadcast of an EM signal, thereby maintaining a constant, preferred level of capacity within the battery of medical device 24.

FIG. 4 is a block diagram illustrating some example components of medical device 24 (e.g., either of medical device 24A or medical device 24B of FIG. 2), which is an example of any of medical devices 14 of FIG. 1, in accordance with one or more examples described in this disclosure. As described above, medical device 24 includes virtually any wearable, implantable, or highly portable medical instrument having an internal rechargeable battery 60 and configured to perform at least one function (e.g., via medical unit 70) pertaining to the treatment of a medical condition of patient 28 (FIG. 2). As shown in FIG. 4, medical device 24 includes processing circuitry 52, memory 54, user interface (UI) 56, telemetry circuitry 58, rechargeable battery 60, receiving antenna 62, tuning circuitry 64, charging circuitry 66, sensor 68, and medical unit 70.

Memory 54 may store program instructions that, when executed by processing circuitry 52, cause processing circuitry 52 to provide the functionality ascribed to medical device 24 throughout this disclosure. In some examples, memory 54 of medical device 24 may store a plurality of parameters, such as parameters pertaining to medical unit 70. As one illustrative example, medical device 24 may include a continuous glucose monitor (CGM) 24A (FIG. 2). In some such examples, medical unit 70 may include a needle and/or other components configured to draw a blood sample from patient 28, and memory 54 may store parameters including values or ranges for preferred glucose levels for comparison to the current sample by processing circuitry 52, as well as previous glucose levels of patient 28 in order to determine a change in patient glucose levels over time. In another illustrative example, medical device 24 may include an insulin pump 24B (FIG. 2). In some such examples, medical unit 70 may include a cannula, an insulin reservoir, a pump, tubing, and/or other components configured to deliver insulin to the body of patient 28, and memory 54 may store parameters pertaining to, for example, an amount or a rate of delivery of glucose to patient 28.

Processing circuitry 52 may retrieve the parameters stored in memory 54, such as in response to receiving a command from controller device 26 via telemetry circuitry 58, to control the functionality of medical unit 70 to treat a medical condition of patient 28. Memory 54 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 52 can take the form one or more microprocessors, DSPs, ASICs, FPGAs, programmable logic circuitry, or the like, and the functions attributed to processing circuitry 52 herein may be embodied as hardware, firmware, software or any combination thereof.

UI 56 may include a button or keypad, lights, a speaker for voice commands, and a display, such as a liquid crystal (LCD) a light emitting diode (LED) display, an organic LED (OLED) display, etc. In some examples the display may be a presence-sensitive display. As discussed in this disclosure, processing circuitry 52 may present and receive information relating to treatment of a medical condition via UI 56. For example, processing circuitry 52 may receive user input via user interface 56. The user input may be entered, for example, by pressing a button on a keypad, entering text, or selecting an icon from a touch screen. The user input may be information indicative of desired parameters for treatment of the patient's medical condition (via medical unit 70) and/or desired parameters for the recharging of rechargeable battery 60 (e.g., a preferred recharging rate) via tuning circuitry 64 and/or charging circuitry 66. For example, patient 28 may indicate, via UI 56, that the patient is currently wearing medical device 24, and accordingly, the power-transfer level should be reduced via the techniques describe above.

Telemetry circuitry 58 includes any suitable hardware, firmware, software or any combination thereof for communicating with another device, such as transmission device 22 (FIG. 2) and patient device 26. Telemetry circuitry 58 may receive communication with the aid of an antenna, which may be internal and/or external to medical device 24, and which may be the same as, or different from, receiving antenna 62. Telemetry circuitry 58 may be configured to communicate with another computing device via wireless communication techniques, or direct communication through a wired connection. Examples of local wireless communication techniques that may be employed to facilitate communication between medical device 26 and another computing device include RF communication according to IEEE 802.11 or Bluetooth specification sets, infrared communication, e.g., according to an IrDA standard, or other standard or proprietary telemetry protocols.

Rechargeable battery 60 delivers operating power to the components of medical device 24, for example, to enable medical unit 70 to perform its functionality to treat a patient medical condition. According to the techniques of this disclosure, as in one or more of the example scenarios described above with respect to FIGS. 1 and 2, processing circuitry 52 is configured to cause tuning circuitry 64 to modify a resonant frequency of receiving antenna 62, such as by modifying an inductor of an RLC circuit or another physical property of an electronic circuit of medical device 24. Similarly, processing circuitry 52 is configured to cause charging circuitry 66 to enable or disable a charging of rechargeable battery 60, such as by opening or closing a switch of charging circuitry. In some examples, charging circuitry 66 may include a transformer or other intermediary electronic components configured to modify a voltage or current of the received electrical signal before delivering the electrical signal to rechargeable battery 60.

According to one or more of the example recharging-management techniques described in this disclosure, medical device 24 is configured to determine a relative proximity of medical device 24 to the body of patient 28. For example, medical device 24 may include at least one sensor 68 configured to generate and output a signal indicative of the relative proximity to patient 28. For example, sensor 68 may include a component configured to indicate a physical contact between medical device 24 and the body of patient 28 (e.g., indicating that medical device 24 is currently being worn by patient 28 or implanted within the body of patient 28). For example, sensor 68 of medical device 24 may include a flex sensor coupled to an exterior of a housing of medical device 24. In some such examples, the flex sensor is configured to bend in response to physical contact with the body of patient 28 while medical device 24 is worn by patient 28. Accordingly, processing circuitry 52 receives an indication of an amount of flex in the flex sensor and determines the physical contact based at least in part on the indication of the amount of flex in the flex sensor. In another example, sensor 68 of medical device 24 includes an optical sensor, wherein physical contact with, or in some examples, proximity to, the body of patient 28 either disrupts (e.g., fully blocks) or at least partially reflects a light-based signal (e.g., a laser) emitted by the optical sensor, and causes the optical sensor to automatically generate an electrical signal indicative of the disrupted and/or reflected light-based signal. In some such examples, processing circuitry 52 receives the electrical signal from the optical sensor and determines the relative proximity and/or physical contact based at least in part on the electrical signal from the optical sensor. In yet another example, sensor 68 includes a skin impedance sensor positioned on the exterior housing of medical device 24, configured to detect or measure an electrical impedance of the area of the patient's skin that contacts the impedance sensor. In some such examples, processing circuitry is configured to receive, from the skin impedance sensor, an indication of the electrical impedance of the skin of patient 28 and determine the physical contact based at least in part on the indication of the electrical impedance of the skin of patient 28.

In some examples, a relative proximity of the body of patient 28 may result in the application of a resistive load to receiving antenna 62. Accordingly, in some examples, sensor 68 includes a receiving-antenna-impedance sensor, configured to measure or monitor a load applied to receiving antenna 62 by the body of patient 28. In some such examples, processing circuitry 52 is configured to determine the relative proximity of medical device 24 to the body of patient 28 by receiving, from the antenna-impedance sensor, an indication of the impedance of receiving antenna 62 resulting from the proximity of the body of patient 28, and determine the relative proximity based at least in part on the indication of the impedance of receiving antenna 62.

As described above, in some examples, UI 56 of medical device 24 includes a user-input mechanism, such as a push-button, enabling a user (e.g., patient 28 or a clinician), to indicate that medical device 24 is currently worn by patient 28. In some such examples, processing circuitry receives the user input and determines the relative proximity (e.g., the physical contact with the body of patient 28) based at least in part on the user input, and then determines the appropriate power-transfer level based on the determined relative proximity.

In some examples, processing circuitry 52 is configured to determine the relative proximity of receiving antenna 62 to the body of patient 28 by determining that receiving antenna 62 is within a threshold distance from (e.g., is sufficiently proximate to) the body of patient 28. In some such examples, processing circuitry 52 is configured to determine a suitable detuning for receiving antenna 62 in order to reduce an amount of electrical power received by receiving antenna 62 from transmission antenna 42 (FIG. 3) to enhance patient safety and comfort, and cause tuning circuitry 64 to detune receiving antenna 62 accordingly.

In other examples, processing circuitry 52 is configured to determine that the receiving antenna 62 is not within a threshold distance from (e.g., is not relatively proximate to) the body of the patient 28. In some such examples, processing circuitry is configured to cause tuning circuitry 64 to tune receiving antenna 62 so as to increase an amount (e.g., a rate or an efficiency) of the electrical power received by the receiving antenna 62 from transmission antenna 42 (FIG. 3). In other such examples, processing circuitry 52 is configured to maintain at least a predetermined minimum threshold (e.g., a predetermined range) of electrical charge in the rechargeable battery 60 by determining that a current level of electrical charge in rechargeable battery 60 is below the minimum threshold, and by causing charging circuitry 66 to activate or enable charging of rechargeable battery 60 via receiving antenna 62 in response to determining that the current level is below the minimum threshold.

In some examples, receiving antenna 62 is detachable from the medical device 24. In other examples, receiving antenna 62 is integrated within a housing of the medical device 24.

In some examples, processing circuitry 52 is configured to periodically alternate between first disabling a medical operation of medical unit 70 and enabling charging circuitry 66 to charge rechargeable battery 60, and second, enabling an operation of the medical unit 70 and disabling charging circuitry 66 from charging rechargeable battery 60, according to a predetermined frequency so as to enable a virtually simultaneous recharging-and-operation of medical device 24.

Figure 5:
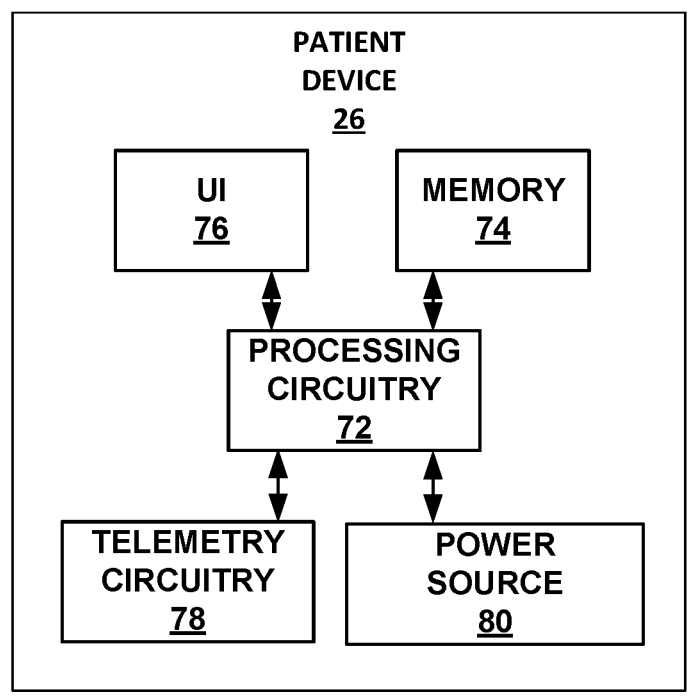
FIG. 5 is a block diagram illustrating an example of the patient controller device of FIG. 2.

FIG. 5 is a block diagram illustrating an example of patient device 26 of FIG. 2, in accordance with one or more examples described in this disclosure. While patient device 26 may generally be described as a hand-held computing device, patient device 26 may be a notebook computer, a cell phone, or a workstation, for example. In some examples, patient device 26 may be a mobile device, such as a smartphone or a tablet computer. In such examples, patient device 26 may execute an application that allows patient device 26 to perform example techniques described in this disclosure. In some examples, patient device 26 may be a specialized (e.g., customized) controller device for communicating with a medical device 24 (FIG. 4), such as either or both of glucose sensor 24A and insulin pump 24B (FIG. 2), and/or transmission device 22 (FIG. 3).

As illustrated in FIG. 5, patient device 26 may include processing circuitry 72, memory 74, user interface 76, telemetry circuitry 78, and power source 80. Memory 74 may store program instructions that, when executed by processing circuitry 72, cause processing circuitry 72 to provide the functionality ascribed to patient device 26 throughout this disclosure.

In some examples, memory 74 of patient device 26 may store a plurality of parameters, such as amounts of insulin to deliver, target glucose level, time of delivery, etc. Processing circuitry 72 (e.g., through telemetry circuitry 78) may output the parameters stored in memory 74 to insulin pump 24B for delivery of insulin to patient 28 (FIG. 2). In some examples, processing circuitry 72 may execute a notification application, stored in memory 74, that outputs notifications to patient 28, such as notification to take insulin, amount of insulin, and time to take the insulin, via user interface 76.

Memory 74 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 72 can take the form one or more microprocessors, DSPs, ASICs, FPGAs, programmable logic circuitry, or the like, and the functions attributed to processing circuitry 72 herein may be embodied as hardware, firmware, software or any combination thereof.

User interface 76 may include a button or keypad, lights, a speaker for voice commands, and a display, such as a liquid crystal (LCD) a light emitting diode (LED) display, an organic LED (OLED) display, etc. In some examples the display may be a presence-sensitive display. As discussed in this disclosure, processing circuitry 72 may present and receive information relating to therapy via user interface 76. For example, processing circuitry 72 may receive patient input via user interface 76. The patient input may be entered, for example, by pressing a button on a keypad, entering text, or selecting an icon from a touch screen. The patient input may be information indicative of food that patient 28 eats, such as for the initial learning phase, whether patient 28 took the insulin (e.g., through the syringe or injection device 30), and other such information.

Telemetry circuitry 78 includes any suitable hardware, firmware, software or any combination thereof for communicating with another device, such as transmission device 22, glucose sensor 24A, and/or insulin pump 24B. Telemetry circuitry 78 may receive communication with the aid of an antenna, which may be internal and/or external to patient device 26. Telemetry circuitry 78 may be configured to communicate with another computing device via wireless communication techniques, or direct communication through a wired connection. Examples of local wireless communication techniques that may be employed to facilitate communication between patient device 26 and another computing device include RF communication according to IEEE 802.11 or Bluetooth specification sets, infrared communication, e.g., according to an IrDA standard, or other standard or proprietary telemetry protocols. Telemetry circuitry 78 may also provide connection with carrier network for access to cloud 26. In this manner, other devices may be capable of communicating with patient device 26.

Power source 80 delivers operating power to the components of patient device 26. In some examples, power source 80 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 26.

Processing circuitry 72 may interface with telemetry circuitry 78 to communicate with glucose sensor 24A, whereby processing circuitry 72 may obtain a current glucose level sensed by sensor 24A in patient 28. Processing circuitry 72 may determine, based on the current glucose level, the projected levels of glucose in patient 28 over a time frame. Processing circuitry 72 may determine whether the projected levels of glucose leave a prescribed range. Processing circuitry 72 may generate, when the projected levels of glucose in patient 28 leave the prescribed range and based on an alert template (which may be stored to memory 74), a graphical alert indicating that the projected levels of glucose will leave a prescribed range.

Processing circuitry 72 may also, as another example, interface with telemetry circuitry 78 to communicate with insulin pump 24B in order to automatically detect an insulin-delivery event indicating that patient 28 has received insulin. Processing circuitry 72 may then automatically (meaning without or with very limited input from patient 28) determine, based on the insulin delivery event, the four hour time frame, switching projection modes from either the longer eight hour time frame or from the shorter two hour time frame.

As described above, processing circuitry 72 of patient device 26 may interface with telemetry circuitry 78 to, for example, activate and deactivate wireless charging of medical device 24, activate and deactivate wireless power broadcast by transmission device 22, indicate to medical device 24 about a relative proximity of medical device 24 to the body of patient 28 such that medical device 24 may determine a suitable tuning for receiving antenna 62, or in some examples, directly indicate to medical device 24 about a suitable tuning frequency for receiving antenna 62.

As one illustrative example, processing circuitry 52 of medical device 24 may monitor the capacity of rechargeable battery 60 and determine when the battery capacity is low (e.g., below a predetermined threshold). In some such examples, processing circuitry 52 may automatically determine, via sensor 68, the relative proximity of the body of patient 28. Processing circuitry 52 may then transmit, via telemetry circuitry 58, a low-battery indication and an indication of the relative proximity to processing circuitry 72 of patient device 26. In response, processing circuitry 72 of patient device 26 may transmit to medical device 24, via telemetry circuitry 78, a suitable tuning frequency for receiving antenna 62. It is to be understood that this is merely a non-limiting example of a communication chain between devices of system 20. Numerous alternative examples exist and are contemplated.

Figure 6:
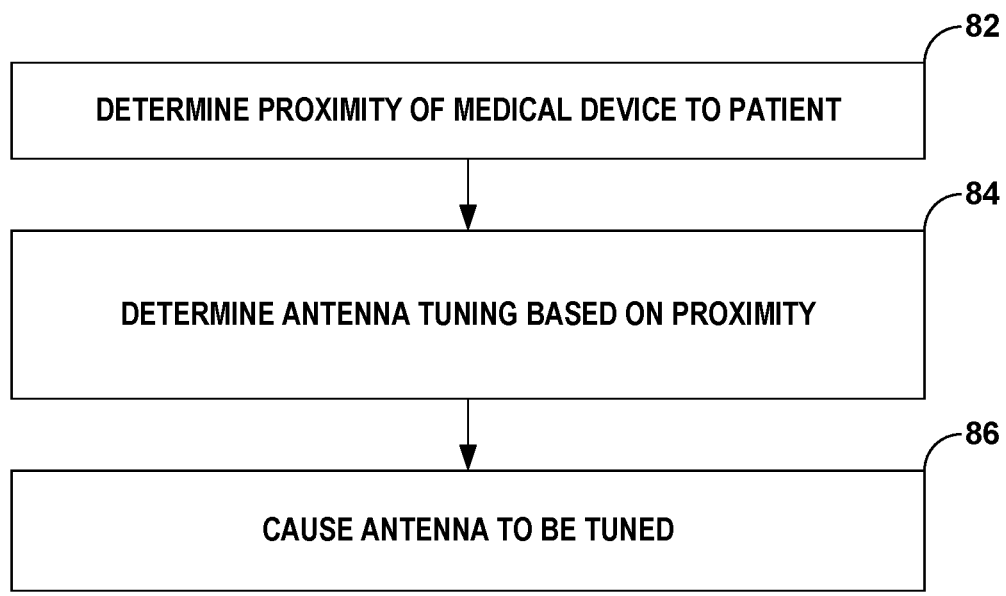
FIG. 6 is a flowchart illustrating an example operation for wirelessly charging a medical device.

FIG. 6 is a flowchart illustrating an example operation for wirelessly charging a medical device, in accordance with the techniques of this disclosure. The techniques of FIG. 6 are described primarily with respect to medical system 20 of FIG. 2 (including medical device 24 detailed in FIG. 4), however, any suitable implantable or wearable medical device may be similarly configured to perform the techniques herein.

Medical device 24 includes at least a rechargeable battery 60 and a receiving antenna 62 configured to wirelessly receive electrical power to charge the rechargeable battery 60. Medical device 24 further includes processing circuitry 52 configured to determine, a relative proximity between medical device 24 (e.g., between receiving antenna 62) and the body of a patient 28 (82). For example, processing circuitry 24 may determine that medical device 24 is currently being worn by patient 28, is currently implanted within patient 28, is within a threshold distance of patient 28, or is outside a threshold distance of patient 28.

The processing circuitry 52 of medical device 24 may then, based on the determined relative proximity, determine a corresponding tuning for the receiving antenna 62 in order to promote, improve, or enhance the comfort and safety of patient 28, the conservation of electrical power, and/or the remaining useful lifespan of the rechargeable battery 60 (84). For example, based on the determined relative proximity of medical device 24 to patient 28, processing circuitry 52 may determine a corresponding suitable wireless-power-transfer level (e.g., power-transfer rate or power-transfer efficiency). As one example, processing circuitry 52 may determine (e.g., select) a relatively reduced power-transfer level in response to determining that medical device 24 is sufficiently proximate to (e.g., is in physical contact with or within a threshold distance of) the body of patient 28. Conversely, processing circuitry 52 may determine (e.g., select) a relatively increased power-transfer level in response to determining that medical device 24 is not proximate to the body of a patient. Processing circuitry 52 may then determine an antenna tuning corresponding to the determined power-transfer level.

Upon determining (e.g., selecting) the corresponding antenna tuning, processing circuitry 52 may then cause receiving antenna 62 to be tuned according to the determined tuning (86). For example, medical device 24 may further include tuning circuitry 64 configured to tune or detune receiving antenna 62 as appropriate, for example, by modifying an inductor of an RLC circuit coupled to receiving antenna 62.

Figure 7:
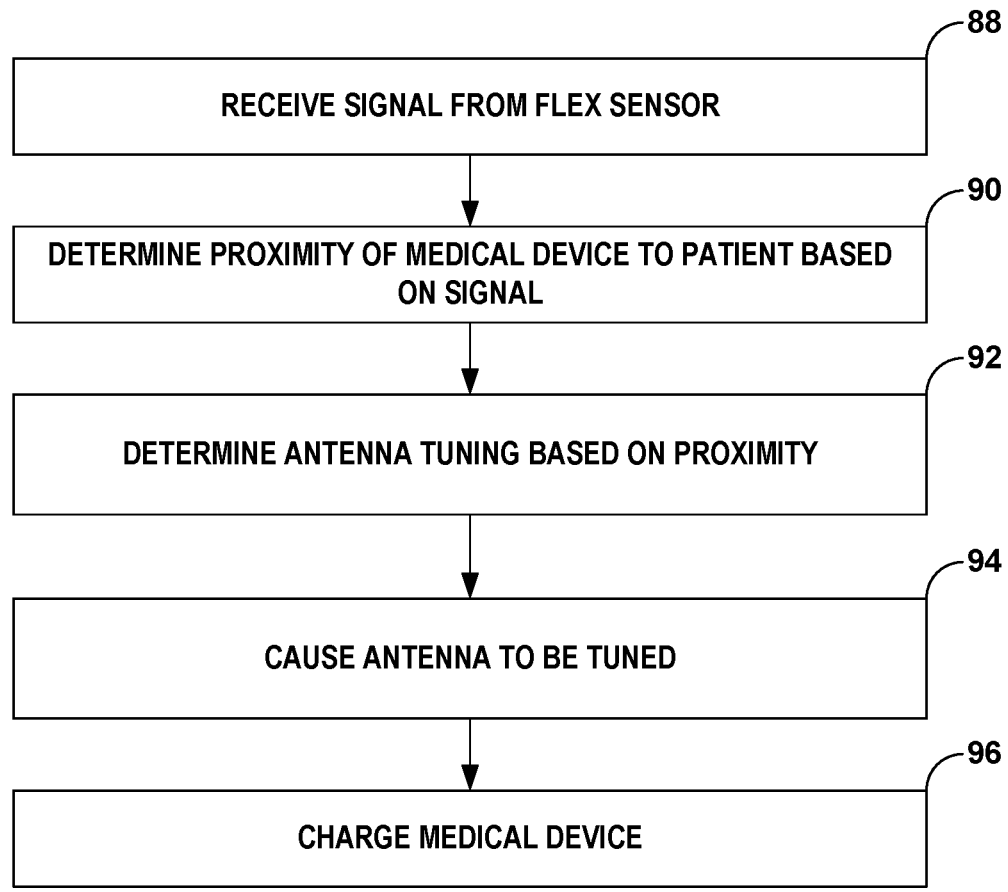
FIG. 7 is a flowchart illustrating another example operation for wirelessly charging a medical device.

FIG. 7 is a flowchart illustrating an example of the operation of FIG. 6, in accordance with the techniques of this disclosure. The techniques of FIG. 7 are described primarily with respect to medical system 20 of FIG. 2 (including medical device 24 detailed further in FIG. 4), however, any suitable implantable or wearable medical device may be similarly configured to perform the techniques herein.

Medical device 24 includes at least a rechargeable battery 60 and a receiving antenna 62 configured to wirelessly receive electrical power to charge the rechargeable battery 60. Medical device 24 further includes a sensor 68, such as a flex sensor coupled to an exterior surface of a housing of medical device 24, configured to generate and output a signal indicative of an amount of flex (e.g., a degree of bending) experienced by the flex sensor in response to a physical contact with the body of patient 28. Medical device 24 further includes processing circuitry 52 configured to receive the signal from the flex sensor (88) and determine, based on the signal, a relative proximity between medical device 24 and the body of the patient 28 (90). For example, processing circuitry 24 may determine, based on the signal from the flex sensor, that medical device 24 is currently being worn by patient 28, is currently implanted within patient 28, is within a threshold distance of patient 28, or is outside a threshold distance of patient 28.

The processing circuitry 52 of medical device 24 may then, based on the determined relative proximity, determine a corresponding tuning for receiving antenna 62 in order to promote, improve, or enhance the comfort and safety of patient 28, the conservation of electrical power, and/or the remaining useful lifespan of rechargeable battery 60 (92). For example, based on the determined relative proximity of medical device 24 to patient 28, processing circuitry 52 may determine a corresponding suitable wireless-power-transfer level (e.g., power-transfer rate or power-transfer efficiency). As one example, processing circuitry 52 may determine (e.g., select) a relatively reduced power-transfer level in response to determining that medical device 24 is sufficiently proximate to (e.g., is in physical contact with or within a threshold distance of) the body of patient 28. Conversely, processing circuitry 52 may determine (e.g., select) a relatively increased power-transfer level in response to determining that medical device 24 is not proximate to the body of a patient. Processing circuitry 52 may then determine an antenna tuning corresponding to the determined power-transfer level.

Upon determining (e.g., selecting) the corresponding antenna tuning, processing circuitry 52 may then cause receiving antenna 62 to be tuned according to the determined tuning (94). For example, medical device 24 may further include tuning circuitry 64 configured to tune or detune receiving antenna 62 as appropriate, for example, by modifying an inductor of an RLC circuit coupled to receiving antenna 62. In some examples, processing circuitry 52 may further cause charging circuitry 66 to activate or enable a charging of rechargeable battery 60, such as by closing an electrical switch to complete a charging circuit (96).

Figure 8:
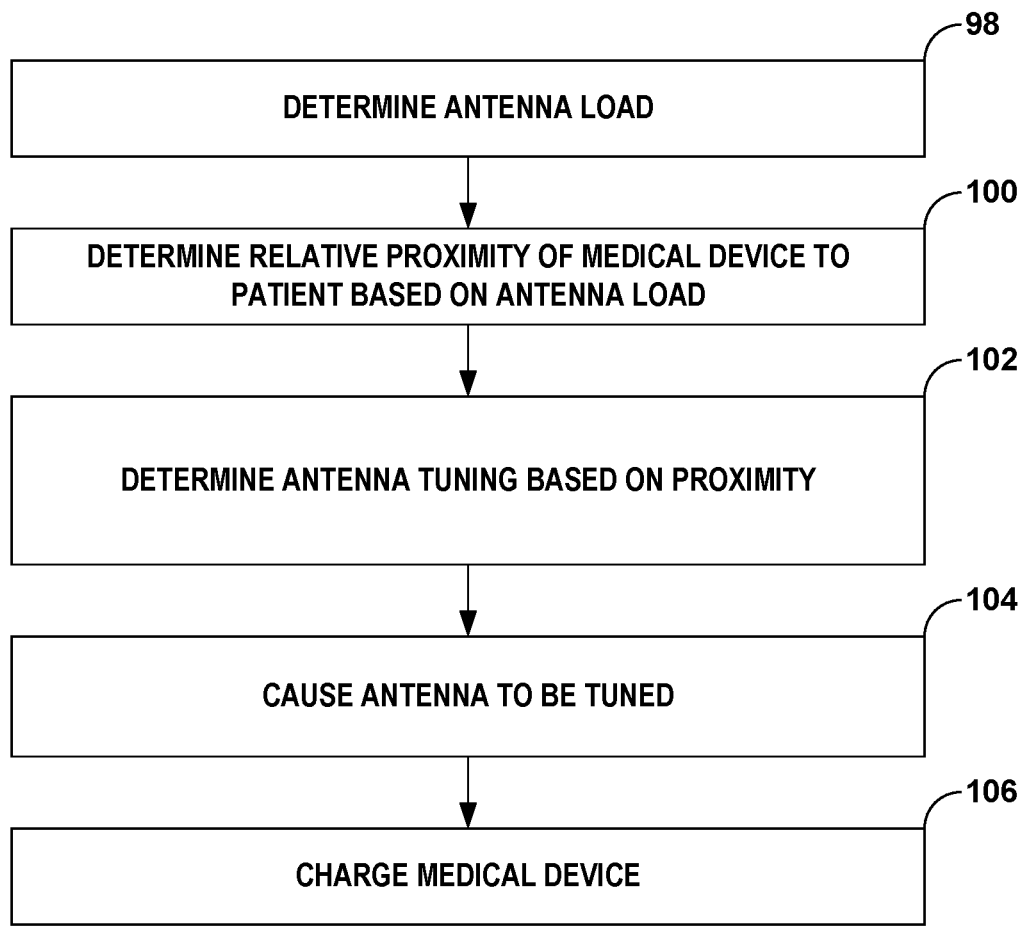
FIG. 8 is a flowchart illustrating an example operation for wirelessly charging a medical device.

FIG. 8 is a flowchart illustrating another example of the operation of FIG. 6, in accordance with the techniques of this disclosure. The techniques of FIG. 8 are described primarily with respect to medical system 20 of FIG. 2 (including medical device 24 detailed further in FIG. 4), however, any suitable implantable or wearable medical device may be similarly configured to perform the techniques herein.

Medical device 24 includes at least a rechargeable battery 60 and a receiving antenna 62 configured to wirelessly receive electrical power to charge the rechargeable battery 60. Medical device 24 further includes a sensor 68, such as a receiving-antenna-impedance sensor, configured to generate and output a signal indicative of a magnitude of an electrically resistive load experienced by receiving antenna 62 and caused by a relative proximity of the body of patient 28 to receiving antenna 62. For example, the generated signal may indicate the degree to which the body of patient 28 is sufficiently near receiving antenna 62 so as to generate an electrical impedance across receiving antenna 62.

Medical device 24 further includes processing circuitry 52 configured to receive the signal from the impedance sensor (98) and determine, based on the signal, a relative proximity between medical device 24 and the body of the patient 28

(100). For example, processing circuitry 24 may determine, based on the signal from the impedance sensor, that medical device 24 is currently being worn by patient 28, is currently implanted within patient 28, is within a threshold distance of patient 28, or is outside a threshold distance of patient 28.

The processing circuitry 52 of medical device 24 may then, based on the determined relative proximity, determine a corresponding tuning for the receiving antenna 62 in order to promote, improve, or enhance the comfort and safety of patient 28, the conservation of electrical power, and/or the remaining useful lifespan of the rechargeable battery 60 (102). For example, based on the determined relative proximity of medical device 24 to patient 28, processing circuitry 52 may determine a corresponding suitable wireless-power-transfer level (e.g., power-transfer rate or power-transfer efficiency). As one example, processing circuitry 52 may determine (e.g., select) a relatively reduced power-transfer level in response to determining that medical device 24 is sufficiently proximate to (e.g., is in physical contact with or within a threshold distance of) the body of patient 28. Conversely, processing circuitry 52 may determine (e.g., select) a relatively increased power-transfer level in response to determining that medical device 24 is not proximate to the body of a patient. Processing circuitry 52 may then determine an antenna tuning corresponding to the determined power-transfer level.

Upon determining (e.g., selecting) the corresponding antenna tuning, processing circuitry 52 may then cause receiving antenna 62 to be tuned according to the determined tuning (104). For example, medical device 24 may further include tuning circuitry 64 configured to tune or detune receiving antenna 62 as appropriate, for example, by modifying an inductor of an RLC circuit coupled to receiving antenna 62. In some examples, processing circuitry 52 may further cause charging circuitry 66 to activate or enable a charging of rechargeable battery 60, such as by closing an electrical switch to complete a charging circuit (106).

Figure 9A:
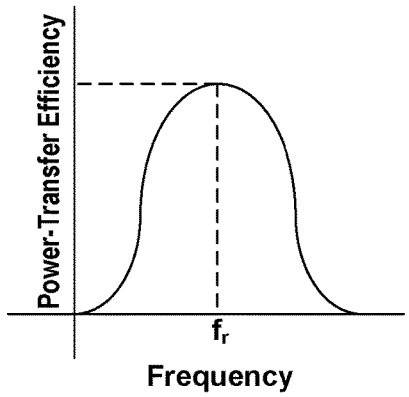
FIGS. 9A-9E are conceptual line graphs illustrating example relationships between electromagnetic transmission frequencies and power-transfer efficiencies.

FIGS. 9A-9E are conceptual line graphs depicting example relationships between wireless-power-transmission frequencies and wireless-power-transfer efficiencies, according to techniques of this disclosure. For instance, FIG. 9A illustrates an example "ideal" power-transfer efficiency as a function of power-transfer frequency. More specifically, FIG. 9A illustrates the relationship between power-transfer frequency and efficiency when a transmission device (e.g., transmission device 22 of FIG. 3) is located directly proximal to (e.g., at zero distance from) a receiving antenna 62 of a medical device 24 (FIG. 4). As shown in FIG. 9A, a theoretical "maximum" power-transfer efficiency is achieved when the receiving antenna 62 is tuned to receive the wireless power at the resonance frequency "$f_r$" of the receiving antenna 62.

Figure 9B:
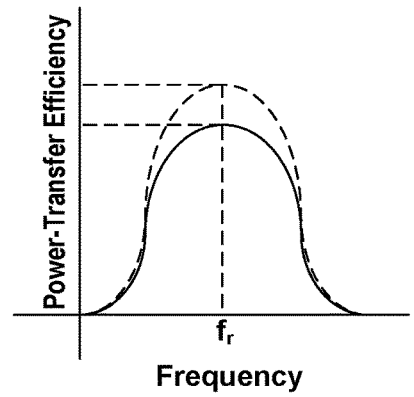

However, as illustrated in FIG. 9B, in many cases, the transmission device 22 will not be located directly proximal to the receiving antenna 62. In such scenarios, some amount of electrical power is lost (e.g., dissipated) with increased distance between the devices, and the power-transfer efficiency decreases from the "ideal" levels shown in FIG. 9A.

Figure 9C:
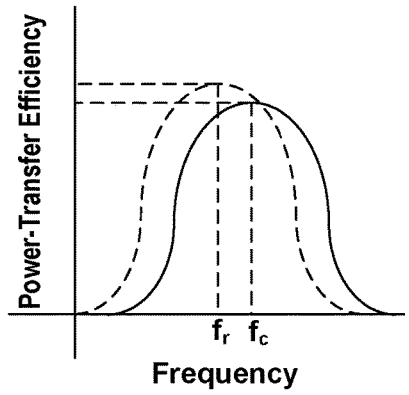

As illustrated in FIG. 9C, the receiving antenna 62 may exhibit a "characteristic" frequency "$f_c$." In theoretical "ideal" scenarios (e.g., FIG. 9A), the characteristic frequency is identical to the resonance frequency of the receiving antenna 62. However, certain scenarios may produce a phase-shift (e.g., frequency shift) between $f_r$ and $f_c$, such as when the body of patient 28 (or other dielectric) is substantially proximal to the receiving antenna 62 to cause a modification in the wireless receiving properties of the antenna. In some such scenarios, as shown in FIG. 9C, if the transmission antenna continues to broadcast at the original resonant frequency $f_r$, some amount of electrical power is lost (e.g., dissipated) due to the "mismatch" between $f_r$ and $f_c$, and the power-transfer efficiency decreases from the "ideal" levels shown in FIG. 9A.

Figure 9D:
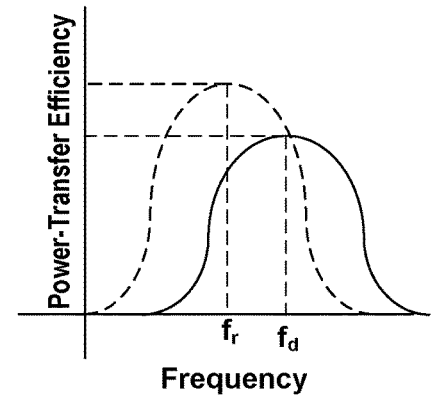

As illustrated in FIG. 9D, according to techniques of this disclosure, receiving antenna 62 may be modified such that the resonance frequency (or characteristic frequency, as appropriate) of receiving antenna 62 is intentionally shifted to a "detuned" frequency "$f_d$" in order to intentionally reduce the power-transfer efficiency to enhance patient comfort and safety.

Figure 9E:
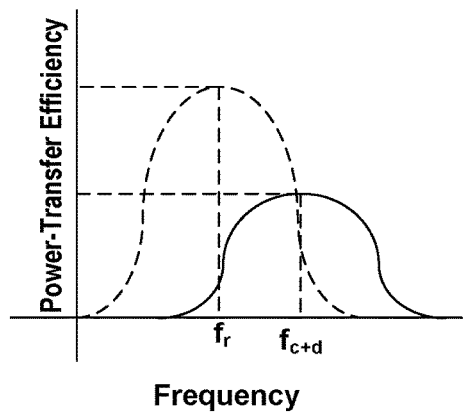

As illustrated in FIG. 9E, the combined effects of (1) transmission loss due to distance traveled through air (FIG. 9B); (2) natural frequency shift due to body proximity (FIG. 9C); and (3) intentional frequency shift of detuned antenna 62 (FIG. 9D) are illustrated, resulting in a substantially reduced power-transfer efficiency as compared to any of the three contributing factors alone. Accordingly, as described above, the intentional detuned frequency $f_d$ of receiving antenna 62 should be selected such that, in the combined presence of all three factors, some minimal or non-negligible amount of electrical power is still wirelessly received by receiving antenna 62, so as to recharge the rechargeable battery of medical device 24.

The following numbered examples illustrate some techniques of this disclosure.

Example 1: In some examples, a medical device includes: a rechargeable battery; a receiving antenna configured to wirelessly receive electrical power from a transmission antenna; charging circuitry configured to recharge the rechargeable battery using the electrical power received by the receiving antenna; and one or more processors configured to: determine a relative proximity of the medical device to a body of a patient; determine, based at least in part on the relative proximity, a tuning for the receiving antenna; and cause the receiving antenna to be tuned according to the determined tuning.

Example 2: In some examples of the medical device of example 1, the medical device includes a continuous glucose monitor (CGM) or an insulin pump.

Example 3: In some examples of the medical device of example 1 or example 2, the receiving antenna is configured to receive the electrical power from the transmission antenna via far-field microwave-spectrum electromagnetic waves.

Example 4: In some examples of the medical device of any of examples 1 through 3, the medical device further includes tuning circuitry configured to modify a resonant frequency of the receiving antenna, wherein causing the receiving antenna to be tuned includes causing the tuning circuitry to modify the resonant frequency of the receiving antenna according to the determined tuning.

Example 5: In some examples of the medical device of any of examples 1 through 4, determining the relative proximity of the medical to the body of the patient includes determining a physical contact between the medical device and the body of the patient.

Example 6: In some examples of the medical device of example 5, the medical device further includes a flex sensor, wherein determining the physical contact between the medical device and the body of the patient includes: receiving an indication of an amount of flex in the flex sensor; and determining the physical contact based at least in part on the indication of the amount of flex in the flex sensor.

Example 7: In some examples of the medical device of example 5 or example 6, the medical device further includes an optical sensor, wherein determining the physical contact between the medical device and the body of the patient includes: receiving a signal from the optical sensor; and determining the physical contact based at least in part on the signal from the optical sensor.

Example 8: In some examples of the medical device of any of examples 5 through 7, the medical device further includes a skin impedance sensor positioned on an exterior housing of the medical device, wherein determining the physical contact between the medical device and the body of the patient further includes receiving, from the skin impedance sensor, an indication of an electrical impedance of a skin of the patient; and determining the physical contact based at least in part on the indication of the electrical impedance of the skin of the patient.

Example 9: In some examples of the medical device of any of examples 1 through 8, the medical device further includes an antenna impedance sensor, wherein determining the relative proximity of the medical device to the body of the patient includes: receiving, from the antenna impedance sensor, an indication of an impedance of the receiving antenna, wherein the impedance of the receiving antenna is based on the relative proximity of the relative proximity of the receiving antenna to the body of the patient; and determining the relative proximity based at least in part on the indication of the impedance of the receiving antenna.

Example 10: In some examples of the medical device of any of examples 1 through 9, the medical device further includes a user-input mechanism, wherein determining the relative proximity of the medical device to body of the patient includes receiving, via the user input mechanism, user input indicative of the relative proximity, and wherein determining the tuning for the receiving antenna includes determining the tuning based at least in part on the user input.

Example 11: In some examples of the medical device of any of examples 1 through 10, determining the relative proximity of the medical device to the body of the patient includes determining that the medical device is within a threshold distance from the body of the patient; and causing the receiving antenna to be tuned according to the determined tuning includes causing the receiving antenna to be tuned in order to reduce a power-transfer efficiency of the receiving antenna.

Example 12: In some examples of the medical device of any of examples 1 through 11, determining the relative proximity of the medical device to the body of the patient includes determining that the medical device is not within a threshold distance from the body of the patient; and causing the receiving antenna to be tuned according to the determined tuning includes tuning the receiving antenna in order to increase a power-transfer efficiency of the receiving antenna.

Example 13: In some examples of the medical device of any of examples 1 through 12, the one or more processors are further configured to maintain a predetermined minimum threshold of electrical charge in the rechargeable battery by: determining that a current level of electrical charge in the rechargeable battery is below the minimum threshold; and causing the charging circuitry to charge the rechargeable battery via the receiving antenna in response to determining that the current level is below the minimum threshold.

Example 14: In some examples of the medical device of any of examples 1 through 13, the receiving antenna is detachable from the medical device.

Example 15: In some examples of the medical device of any of examples 1 through 13, the receiving antenna is integrated within a housing of the medical device.

Example 16: In some examples of the medical device of any of examples 1 through 15, the one or more processors are further configured to periodically alternate between causing the charging circuitry to charge the rechargeable battery and enabling an operation of the medical device.

Example 17: In some examples, a system for wirelessly charging a medical device includes the medical device and a wireless-power-transfer device including a transmission antenna. The medical device includes: a rechargeable battery; a receiving antenna configured to wirelessly receive electrical power from the transmission antenna; charging circuitry configured to recharge the rechargeable battery using the electrical power received by the receiving antenna; and one or more processors configured to: determine a relative proximity of the medical device to a body of a patient; determine, based at least in part on the relative proximity, a tuning for the receiving antenna; and cause the receiving antenna to be tuned according to the determined tuning.

Example 18: In some examples of the system of example 17, the wireless-power-transfer device is configured to transmit the electrical power from the transmission antenna via far-field microwave-spectrum electromagnetic waves.

Example 19: In some examples, a processor-implemented method for wirelessly charging a medical device via a receiving antenna includes: determining a relative proximity of a medical device to a body of a patient; determining, based at least in part on the relative proximity, a corresponding tuning for the receiving antenna of the medical device; and causing the receiving antenna to be tuned according to the corresponding tuning.

Example 20: In some examples of the method of example 19, determining the relative proximity of the medical device to the body of the patient includes determining that the medical device is within a threshold distance from the body of the patient, and causing the receiving antenna to be tuned according to the determined tuning includes tuning the receiving antenna in order to reduce a power-transfer efficiency of the receiving antenna.

Example 21: In some examples, one or more non-transitory processor-readable storage media store instructions that, when executed by one or more processors, cause performance of: determining a relative proximity of a medical device to a body of a patient; determining, based at least in part on the relative proximity, a tuning for a receiving antenna of the medical device; and causing the receiving antenna to be tuned according to the determined tuning.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general-purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 32 of transmission device 22, one or more processors of medical device(s) 24, one or more processors of patient device 26, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A medical device comprising:
a rechargeable battery;
a receiving antenna configured to wirelessly receive electrical power from a transmission antenna;
charging circuitry configured to recharge the rechargeable battery using the electrical power received by the receiving antenna; and
one or more processors configured to:
determine a relative proximity of the medical device to a body of a patient;
determine a power-transfer efficiency based on the relative proximity of the medical device to the body of the patient;
determine, based at least in part on the relative proximity and the power-transfer efficiency, a tuning for the receiving antenna that is safe for the patient; and
cause the receiving antenna to be tuned according to the determined tuning.

2. The medical device of claim 1, wherein the medical device comprises a continuous glucose monitor (CGM) or an insulin pump.

3. The medical device of claim 1, wherein the receiving antenna is configured to receive the electrical power from the transmission antenna via far-field microwave-spectrum electromagnetic waves.

4. The medical device of claim 1, further comprising tuning circuitry configured to modify a resonant frequency of the receiving antenna, wherein causing the receiving antenna to be tuned comprises causing the tuning circuitry to modify the resonant frequency of the receiving antenna according to the determined tuning.

5. The medical device of claim 1, wherein determining the relative proximity of the medical to the body of the patient comprises determining a physical contact between the medical device and the body of the patient.

6. The medical device of claim 5, further comprising a flex sensor, wherein determining the physical contact between the medical device and the body of the patient comprises:
receiving an indication of an amount of flex in the flex sensor; and
determining the physical contact based at least in part on the indication of the amount of flex in the flex sensor.

7. The medical device of claim 5, further comprising an optical sensor, wherein determining the physical contact between the medical device and the body of the patient comprises:
receiving a signal from the optical sensor; and
determining the physical contact based at least in part on the signal from the optical sensor.

8. The medical device of claim 5, further comprising a skin impedance sensor positioned on an exterior housing of the medical device, wherein determining the physical contact between the medical device and the body of the patient comprises:
receiving, from the skin impedance sensor, an indication of an electrical impedance of a skin of the patient; and
determining the physical contact based at least in part on the indication of the electrical impedance of the skin of the patient.

9. The medical device of claim 1, further comprising an antenna impedance sensor, wherein determining the relative proximity of the medical device to the body of the patient comprises:
receiving, from the antenna impedance sensor, an indication of an impedance of the receiving antenna, wherein the impedance of the receiving antenna is based on the relative proximity of the relative proximity of the receiving antenna to the body of the patient; and
determining the relative proximity based at least in part on the indication of the impedance of the receiving antenna.

10. The medical device of claim 1, further comprising a user-input mechanism, wherein determining the relative proximity of the medical device to body of the patient comprises receiving, via the user input mechanism, user input indicative of the relative proximity, and wherein determining the tuning for the receiving antenna comprises determining the tuning based at least in part on the user input.

11. The medical device of claim 1:
wherein determining the relative proximity of the medical device to the body of the patient comprises determining that the medical device is within a threshold distance from the body of the patient; and
wherein causing the receiving antenna to be tuned according to the determined tuning comprises causing the receiving antenna to be tuned in order to reduce a power-transfer efficiency of the receiving antenna.

12. The medical device of claim 1:
wherein determining the relative proximity of the medical device to the body of the patient comprises determining that the medical device is not within a threshold distance from the body of the patient; and
wherein causing the receiving antenna to be tuned according to the determined tuning comprises tuning the receiving antenna in order to increase a power-transfer efficiency of the receiving antenna.

13. The medical device of claim 1, wherein the one or more processors are further configured to maintain a predetermined minimum threshold of electrical charge in the rechargeable battery by:
determining that a current level of electrical charge in the rechargeable battery is below the minimum threshold; and
causing the charging circuitry to charge the rechargeable battery via the receiving antenna in response to determining that the current level is below the minimum threshold.

14. The medical device of claim 1, wherein the receiving antenna is detachable from the medical device.

15. The medical device of claim 1, wherein the receiving antenna is integrated within a housing of the medical device.

16. The medical device of claim 1, wherein the one or more processors are further configured to periodically alternate between causing the charging circuitry to charge the rechargeable battery and enabling an operation of the medical device.

17. A system for wirelessly charging a medical device, the system comprising:
a wireless-power-transfer device comprising a transmission antenna; and
the medical device comprising:
a rechargeable battery;
a receiving antenna configured to wirelessly receive electrical power from the transmission antenna;
charging circuitry configured to recharge the rechargeable battery using the electrical power received by the receiving antenna; and
one or more processors configured to:
determine a relative proximity of the medical device to a body of a patient;
determine a power-transfer efficiency based on the relative proximity of the medical device to the body of the patient;
determine, based at least in part on the relative proximity and the power-transfer efficiency, a tuning for the receiving antenna that is safe for the patient; and
cause the receiving antenna to be tuned according to the determined tuning.

18. The system of claim 17, wherein the wireless-power-transfer device is configured to transmit the electrical power from the transmission antenna via far-field microwave-spectrum electromagnetic waves.

19. The system of claim 17, wherein determining the relative proximity of the medical device to the body of the patient comprises determining that the medical device is within a threshold distance from the body of the patient, and wherein causing the receiving antenna to be tuned according to the determined tuning comprises tuning the receiving antenna in order to reduce a power-transfer efficiency of the receiving antenna.

20. One or more non-transitory processor-readable storage media storing instructions that, when executed by one or more processors, cause performance of:
determining a relative proximity of a medical device to a body of a patient, wherein determining the relative proximity comprises determining whether the medical device is being worn by the patient;
determining, based at least in part on the relative proximity and power-transfer efficiency, a tuning for a receiving antenna of the medical device that is safe for the patient; and
causing the receiving antenna to be tuned according to the determined tuning.

* * * * *